(12) United States Patent
Mundschau et al.

(10) Patent No.: US 8,911,417 B2
(45) Date of Patent: Dec. 16, 2014

(54) DIAPER WITH UMBILICAL FEATURE

(71) Applicant: Kimberly-Clark Worldwide, Inc., Neenah, WI (US)

(72) Inventors: Chantel Spring Mundschau, Weyauwega, WI (US); Kusum Gosain, Woodbury, MN (US); Shannon Kathleen Melius, Appleton, WI (US); John Timothy Hahn, Merrill, WI (US); Vipula Jitendra Tailor, Alpharetta (GB); Earl David Brock, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 13/937,717

(22) Filed: Jul. 9, 2013

(65) Prior Publication Data

US 2013/0296821 A1   Nov. 7, 2013

Related U.S. Application Data

(63) Continuation of application No. 11/111,531, filed on Apr. 20, 2005, now Pat. No. 8,506,546.

(51) Int. Cl.
*A61F 13/15* (2006.01)

(52) U.S. Cl.
USPC ............ 604/385.09; 604/385.31; 604/385.11; 604/385.01; 604/391; 604/394

(58) Field of Classification Search
USPC .......... 604/385.09, 402, 385.11, 385.31, 387, 604/389, 391, 394
See application file for complete search history.

(56) References Cited

U.S. PATENT DOCUMENTS

| | | | |
|---|---|---|---|
| 2,525,396 A | 10/1950 | Brennan | |
| 2,684,677 A | 7/1954 | Pinney | |
| 2,738,789 A | 3/1956 | Foxworthy | |
| 3,141,461 A | 7/1964 | Farris | |
| 3,623,488 A | 11/1971 | Nakayama | |
| 4,230,113 A | 10/1980 | Mehta | |
| 4,675,015 A * | 6/1987 | Brown ..................... | 604/385.09 |
| 4,769,023 A * | 9/1988 | Goebel et al. ............ | 604/385.21 |
| 4,795,452 A | 1/1989 | Blaney et al. | |
| 4,801,298 A | 1/1989 | Sorenson et al. | |
| 4,944,733 A | 7/1990 | Casale | |
| D311,582 S | 10/1990 | Gilchrist | |
| 5,064,421 A | 11/1991 | Tracy | |
| D334,978 S | 4/1993 | Rutherford | |
| D341,422 S | 11/1993 | Cosentino | |

(Continued)

FOREIGN PATENT DOCUMENTS

| | | |
|---|---|---|
| EP | 0 155 636 A2 | 9/1985 |
| FR | 2 604 867 A1 | 4/1988 |

(Continued)

*Primary Examiner* — Jacqueline F. Stephens
(74) *Attorney, Agent, or Firm* — Kimberly-Clark Worldwide, Inc.

(57) ABSTRACT

A diaper having a front portion with at least one line of weakness adapted to be torn and at least one umbilical cover defined in part by the at least one line of weakness. The at least one umbilical cover is moveable from a starting position to an anchored position upon tearing the at least one line of weakness. The diaper has at least one umbilical cover anchor adapted to maintain the at least one umbilical cover in the anchored position.

16 Claims, 13 Drawing Sheets

(56) References Cited

U.S. PATENT DOCUMENTS

| | | |
|---|---|---|
| 5,295,986 A | 3/1994 | Zehner et al. |
| 5,304,158 A | 4/1994 | Webb |
| 5,306,267 A | 4/1994 | Hahn et al. |
| 5,318,555 A | 6/1994 | Siebers et al. |
| 5,358,500 A | 10/1994 | Lavon et al. |
| 5,366,453 A | 11/1994 | Zehner et al. |
| 5,406,964 A | 4/1995 | Calleja |
| 5,489,282 A | 2/1996 | Zehner et al. |
| 5,599,338 A | 2/1997 | Enloe |
| 5,669,897 A | 9/1997 | Lavon et al. |
| 5,707,364 A | 1/1998 | Coates |
| 5,814,037 A | 9/1998 | Coates |
| 5,836,930 A | 11/1998 | Lantz et al. |
| D403,400 S | 12/1998 | Bernard et al. |
| D403,401 S | 12/1998 | Bernard et al. |
| D403,402 S | 12/1998 | Dreier et al. |
| 5,989,236 A * | 11/1999 | Roe et al. .......... 604/385.04 |
| 6,102,899 A * | 8/2000 | Yimin ................ 604/385.01 |
| 6,110,157 A | 8/2000 | Schmidt |
| D452,315 S | 12/2001 | Coates |
| 6,423,047 B1 | 7/2002 | Webster |
| 6,482,194 B1 | 11/2002 | Putzer |
| 6,626,879 B1 | 9/2003 | Ashton et al. |
| 7,641,641 B2 * | 1/2010 | Ramshak .......... 604/385.01 |
| 7,947,028 B2 * | 5/2011 | Cohen et al. ...... 604/385.09 |
| 2005/0113778 A1* | 5/2005 | Johansson et al. ... 604/385.01 |
| 2006/0212013 A1 | 9/2006 | Cohen et al. |
| 2006/0241558 A1 | 10/2006 | Ramshak |

FOREIGN PATENT DOCUMENTS

| | | |
|---|---|---|
| GB | 1 133 502 A | 11/1968 |
| JP | 03-236839 A | 10/1991 |
| WO | WO 03/009792 A1 | 2/2003 |

* cited by examiner

DIAPER WITH UMBILICAL FEATURE

BACKGROUND OF THE INVENTION

Absorbent articles, such as disposable diapers, have generally included topsheets, backsheets, and absorbent structures. Some diapers specifically designed for newborn children have further included V-shaped or U-shaped notches cut away from the front waist section of the diaper to minimize contact with the umbilical region of newborn children. However, these diapers have not allowed the caregiver the option of using the umbilical feature.

Other diapers that provide an umbilical feature have included various perforations and separable panels to expose the umbilical region but have not included any means of keeping the panels from contacting, and potentially irritating, the umbilical region. Yet other diapers have required pieces or parts of the diaper to be removed. In these designs, the inconvenience of removing and disposing of a separate part may be less desirable to caregivers.

As a result, there is a continued need for disposable diapers, particularly designed for newborns, which include an optional umbilical feature that does not require the disposal of removable parts and maintains an area that is free of diaper components and minimizes contact and irritation with the umbilical cord and/or navel.

SUMMARY OF THE INVENTION

In response to the discussed difficulties and problems encountered previously, the present invention provides a diaper having a front portion, an outer cover, a liner and an absorbent core positioned between the outer cover and the liner. The front portion has a first line of weakness adapted to be torn, the first line of weakness including one or more rows of perforations. The front portion has a first umbilical cover defined in part by the first line of weakness. The first umbilical cover is moveable from a starting position to an open position upon tearing the diaper at the first line of weakness. The diaper also includes at least one of a front fastener joined to the outer cover in the front portion and a front waist elastic joined to the liner in the front portion. The at least one of the front fastener and the front waist elastic has at least two bonded portions and at least one unbonded portion. The at least one unbonded portion is located between the at least two bonded portions and defines a first pocket. The first pocket is adapted to accept and maintain at least a portion of the first umbilical cover in the open position.

In another embodiment, the present invention provides a diaper having a front portion, an outer cover, a liner, and an absorbent core positioned between the outer cover and the liner. The front portion has a line of weakness adapted to be torn. The line of weakness includes at least one row of perforations. The front portion has a pair of umbilical covers defined in part by the line of weakness. The umbilical covers are moveable from a starting position to an open position upon tearing the diaper at the line of weakness. The pair of umbilical covers is defined in part by the line of weakness. The diaper further includes a front fastener located in the front portion. The front fastener has umbilical cover anchors joined thereto. The umbilical cover anchors are adapted to maintain the umbilical covers in the open position.

In various embodiments, the at least one umbilical cover anchor may be joined with the umbilical cover when the umbilical cover is in the starting position. In other embodiments, the at least one umbilical cover may be free of umbilical cover anchors when the umbilical cover is in the starting position.

In various embodiments, the umbilical cover anchor may include a hook material. In various embodiments, the front fastener may be made of loop material. In various embodiments, an umbilical cover anchor including hook material may be adapted to engage a front fastener including loop material to anchor the umbilical cover in the anchored position.

In various embodiments, the diaper may include a front fastener located in the front portion and an outer cover. The front fastener may be joined with the outer cover at two or more bonded portions. The front fastener may have one or more unbonded portions located between the two or more bonded portions. The one or more unbonded portions define at least one pocket and are adapted to maintain the umbilical cover in the anchored position.

In various embodiments, the diaper may include a front waist elastic located in the front portion and a bodyside liner. The front waist elastic may be joined with the bodyside liner at two or more bonded portions. The front waist elastic may have one or more unbonded portions located between the two or more bonded portions. The one or more unbonded portions define one or more pockets adapted to maintain the at least one umbilical cover in the anchored position.

In various embodiments, the diaper may include at least one fold line, at least one folding guide, at least one stabilizer and/or at least one line of weakness indicator.

In various embodiments, the at least one line of weakness may be comprised of at least one row of perforations extending at least partially through the outer cover, the front waist elastic and/or the bodyside liner. The at least one line of weakness may extend in a longitudinal direction from the front waist edge to the front fastener.

The present invention also teaches a method of providing a system to create an umbilical relief area in a diaper. The method includes providing a diaper having a front portion. The front portion has at least one line of weakness adapted to be torn. The diaper also has at least one umbilical cover defined in part by the at least one line of weakness. The at least one umbilical cover is moveable from a starting position to an anchored position upon tearing the at least one line of weakness. The diaper also has at least one umbilical cover anchor adapted to maintain the at least one umbilical cover in the anchored position. The method further includes providing instructions to a caregiver, desiring to utilize the umbilical feature, to tear the diaper along the at least one line of weakness, to move the at least one umbilical cover from the starting position to the anchored position and to maintain the umbilical cover in the anchored position by utilizing the umbilical cover anchor. The diaper provided in this method may, in various embodiments, include at least one fold line and at least one folding guide and the instructions inform the caregiver to fold the umbilical cover along one of the fold lines after tearing the diaper along the at least one line of weakness.

DETAILED DESCRIPTION OF THE DRAWINGS

The absorbent articles of the present invention will be described in terms of diapers adapted to be worn by babies, particularly newborns, about the lower torso. The umbilical feature of the present invention will be described in terms of providing relief to the healing umbilical area of newborns. However, the absorbent articles of the present invention may also be applicable to other articles such as adult incontinent products, training pants, feminine care products and the like, to provide a relief area such as after surgery for example.

The diaper umbilical feature of the present invention is an improvement over the umbilical features of the prior art diapers in several ways. First, the umbilical feature is optional. The caregiver may utilize the umbilical feature when the umbilical cord is still attached and/or the navel is sensitive to minimize contact between the diaper and the umbilical cord and/or navel. The caregiver may alternatively choose to use the diaper without exposing the navel after the umbilical cord has detached. Second, the present invention does not include a removable umbilical notch and thus requires no disposal of removable parts like diapers with a removable umbilical notch. Finally, the present invention is an improvement over the prior art because the caregiver can choose to expose the umbilical cord and secure the umbilical feature in an anchored position thereby maintaining an umbilical relief area once created.

Figure 1:
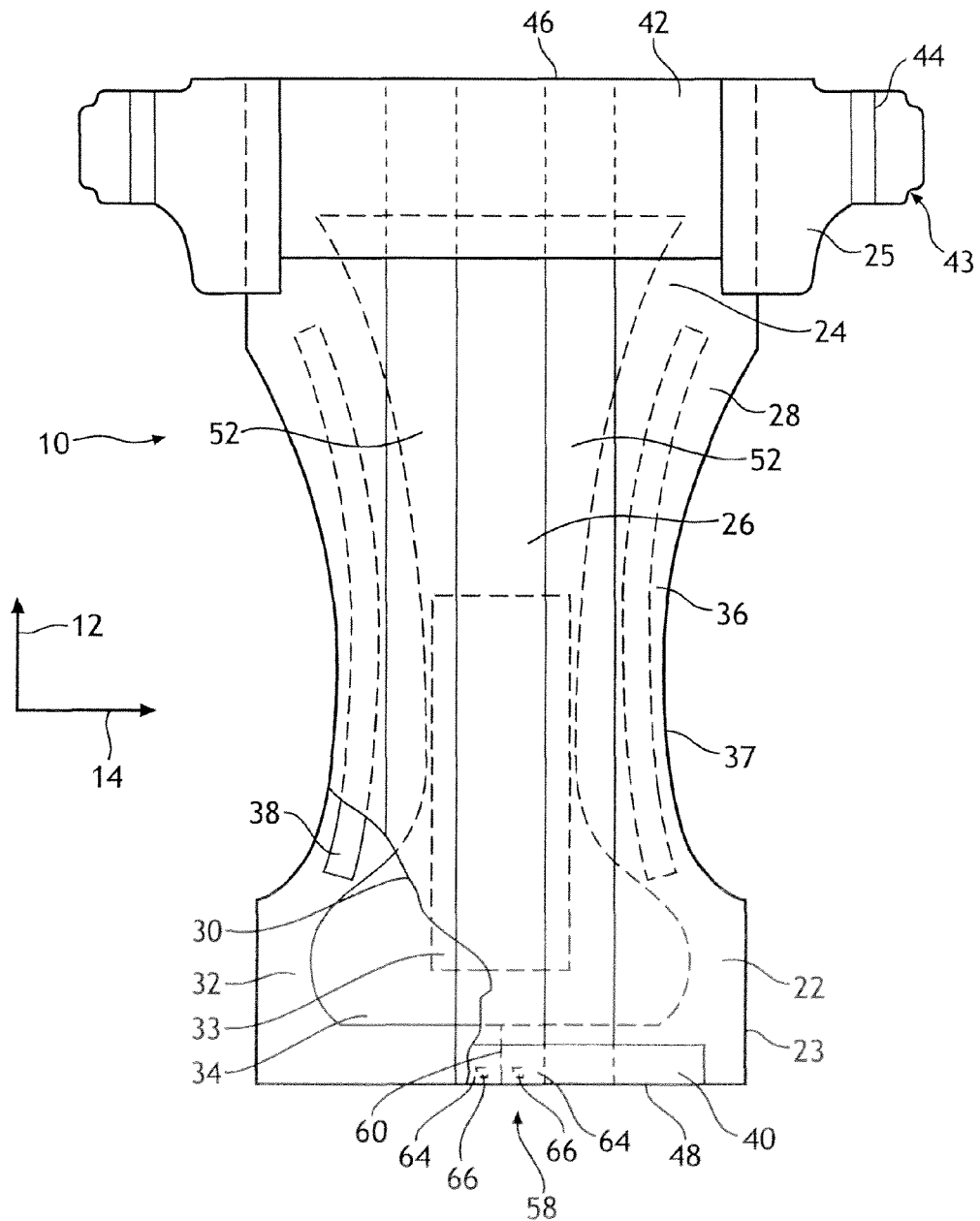
FIG. 1 representatively illustrates a partially cut away, top plan view of an absorbent article in a stretched and laid flat condition with the surface of the article that contacts the skin of the wearer facing the viewer and with the umbilical feature in the closed condition.

FIG. 1 representatively illustrates a diaper 10 of the present invention in an unfastened condition. Portions of the diaper 10 are cut away to illustrate underlying structure. The surface of the diaper which contacts the wearer is facing the viewer in FIG. 1. The diaper 10 has a longitudinal direction 12 and a lateral direction 14. In the longitudinal direction 12, the diaper 10 defines a front portion 22, a back portion 24, and a crotch portion 26 connecting the front portion 22 and the back portion 24. The diaper 10 includes a bodyside liner 30, an outer cover 32 and an absorbent core 34 located between the bodyside liner 30 and the outer cover 32. The front portion 22 may include, at least partially, one or more front ears 23. The back portion 24 may include, at least partially, one or more back ears 25. The front ears 23 and/or the back ears 25 may be formed from extensions of the bodyside liner 30, the outer cover 32, combinations of both the bodyside liner 30 and the outer cover 32, or by the addition of one or more separate components as is known in the art.

The front portion 22 includes an umbilical feature 58. The umbilical feature 58 includes at least one line of weakness 60, at least one umbilical cover 64 and at least one umbilical cover anchor 66. The at least one umbilical cover 64 is defined in part by the at least one line of weakness 60. The umbilical feature 58 may optionally include one or more fold lines 62, one or more folding guides 70, and/or one or more line of weakness indicators 72.

The diaper 10 also includes a fastener system 43. The fastener system 43 includes one or more back fasteners 44 and one or more front fasteners 45 (see FIG. 2 for example). Portions of the fastener system 43 may be included in the front portion 22, the back portion 24, or both. The fastener system 43 is adapted to secure the diaper 10 about the waist of a wearer and maintain the diaper 10 in place during use.

The diaper 10 may also include a surge portion 33 joined to the absorbent core 34 and/or the bodyside liner 30. As used herein, reference to a front portion refers to that part of the diaper which is generally located on the front of a wearer when in use. Reference to the back portion refers to the portion of the diaper generally located at the back of the wearer when in use, and reference to the crotch portion refers to that portion which is generally located between the legs of the wearer when in use.

The crotch portion 26 has opposite longitudinal side portions 28 which may include a pair of elasticized, longitudinally-extending leg cuffs 36. The leg cuffs 36 are generally adapted to fit about the legs of a wearer in use and serve as a mechanical barrier to the lateral flow of body exudates. The leg cuffs 36 may be elasticized by a pair of leg elastics 38. The diaper 10 may further include a front waist elastic 40 and/or a back waist elastic 42.

The back portion 24 may have a straight back waist edge 46, an arcuate back waist edge 46, or a back waist edge 46 cut in other shapes as are known in the art. The front portion 22 may have a straight front waist edge 48, an arcuate front waist edge 48, or a front waist edge 48 cut in other shapes as are known in the art. As used herein, the term "straight" refers to edges that are substantially free from curves, bends, angles, notches or irregularities.

The diaper 10 may also include a pair of containment flaps 52 that may extend longitudinally along the diaper 10 and may also be adapted to provide a barrier to the flow of body exudates. It should be recognized that individual components of the diaper 10 may be optional depending upon the intended use of the diaper 10. In some embodiments, the diaper 10 may also include one or more stabilizers 74 adapted to resist rollover of the front waist edge 48 and/or the back waist edge 46. The stabilizers 74 may include one or more additional elements joined to the diaper 10. For example, the stabilizers 74 may include resilient materials, elastomeric materials, adhesives, plastics, or any other rigid or semi-rigid material or materials adapted to provide stability. Alternatively, the stabilizers 74 may be provided by thermally deforming one or more of the bodyside liner 30, outercover 32, front waist elastic 40, back waist elastic 42, or back ears 25, or combinations thereof to provide stability. Alternatively, the stabilizers 74 may be provided by utilizing stiff, thick or dense materials such as the bodyside liner 30, outercover 32, front waist elastic 40, back waist elastic 42, or back ears 25, or combinations thereof to provide stability. The stabilizers 74 may be particularly useful when located proximate the one or more lines of weakness 60 to maintain the front waist edge 48 in position, and resist rollover, before and/or after the one or more lines of weakness 60 have been torn.

The bodyside liner 30 of the diaper 10, as representatively illustrated in FIG. 1, suitably presents a body facing surface which is intended to be worn adjacent the body of the wearer and is compliant, soft feeling and nonirritating to the wearer's skin. Further, the bodyside liner 30 may be less hydrophilic than the absorbent core 34 and may be sufficiently porous to be liquid permeable. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearers skin from fluids held in the composite absorbent core 34.

The outer cover 32 of the diaper 10 suitably presents a garment facing surface which is intended to be worn adjacent the clothing of the wearer. The outer cover 32 may be a polyethylene film. Alternative constructions of the outer cover 32 may comprise a woven or non-woven fibrous web layer which has been totally or partially constructed or treated to impart a desired level of liquid impermeability to selected regions of the backsheet that are adjacent or proximate the absorbent core 34. For example, a clothlike backsheet may be composed of polypropylene spunbond fabric which is laminated and thermally bonded to a stretch-thinned polypropylene film. The outer cover 32 may optionally include a microporous, "breathable" material which permits vapors to escape from diaper 10 while still preventing liquid exudates from passing through. For example, the outer cover 32 may be composed of a microporous polymer film or a nonwoven fabric which has been coated or otherwise treated to impart a desired level of liquid impermeability. The outer cover 32 can also be embossed or otherwise provided with a matte finish to exhibit a more aesthetically pleasing appearance. The size of outer cover 32 is typically determined by the size of diaper 10 and the exact diaper design selected.

The bodyside liner 30 and outer cover 32 are generally joined in facing relationship with the absorbent core 34 located therebetween. The bodyside liner 30 and the outer cover 32 may be joined to each other around the outer periphery of the diaper 10 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

The leg cuffs 36 are suitably formed by portions of the outer cover 32, and/or bodyside liner 30, which extend beyond the longitudinal sides of the absorbent core 34. Alternatively, the leg cuffs 36 can be formed from separate materials joined to the outer cover 32 and/or bodyside liner 30. In some embodiments, the leg cuffs 36 may have an arcuate shape resulting from a leg cut out 37. In other embodiments, the leg cuffs 36 may have a generally straight leg cut out 37.

The leg cuffs 36 may include leg elastics 38. Front waist elastics 40 and/or back waist elastic 42 may also be provided. The leg elastics 38 may be arranged to draw and hold the diaper 10 against the legs of the wearer. The waist elastics 40 and 42 may also be arranged to draw and hold the diaper 10 against the wearer, particularly at the waist. Materials suitable for use in forming leg elastics 38 and/or waist elastics 40 and 42 are known to those skilled in the art. Exemplary of such materials are strands or ribbons of a polymeric, elastomeric material which are adhered to the diaper 10 in a stretched position, or which are attached to the diaper while the diaper is pleated, such that elastic constrictive forces are imparted to the diaper 10. The leg elastics 38 and waist elastics 40 and 42 may have any configuration which provides the desired performance. The leg elastics 38 may be generally straight or optionally curved to more closely fit the contours of the legs and buttocks of the wearer and better contain bodily exudates. The leg elastics 38 and waist elastics 40 and 42 may be attached to the diaper 10 in any of several ways which are well known to those skilled in the art. For example, the elastics may be joined to the diaper 10 by ultrasonic bonding, thermal bonding, adhesive bonding, and the like, and combinations thereof.

The front ears 23 and/or the back ears 25 are suitably formed by portions of the outer cover 32, and/or bodyside liner 30, which extend beyond the longitudinal sides of the absorbent core 34. For example, in FIG. 1, the front ears 23 are illustrated as portions of both the outer cover 32 and the bodyside liner 30. Alternatively, the front ears 23 and/or back ears 25 could be formed from separate materials which are joined to the outer cover 32 and/or bodyside liner 30. For example, in FIG. 1, the back ears 25 are illustrated as separate pieces of material attached to the bodyside liner 30.

The front ears 23 and/or the back ears 25 of the present invention may comprise one or more materials joined together to form a composite ear as is well known in the art. One or more of the materials may be elastomeric. Elastomeric ears can be formed from any type of an elastomeric material capable of performing as described herein. Generally, the elastomeric material will be stretchable in at least one direction. Preferably, the elastomeric material will be stretchable in two directions. When the elastomeric material is stretchable in a single direction, the stretch direction of the elastomeric material will be oriented so as to provide elastomeric forces which tend to pull the front and back portions of the diaper towards one another such that the diaper is maintained about the waist of a wearer.

The elastomeric material may be an inherently elastomeric material, that is, one which is formed in an elastomeric state, or may be rendered elastomeric through processing subsequent to formation. For example, the elastomeric material may be heat or pressure activated. In particular embodiments of the invention, portions of the ears may comprise an elastomeric material, such as a stretch-bonded-laminate (SBL) material, a neck-bonded-laminate (NBL) material, an elastomeric film, an elastomeric foam material, or the like.

In some embodiments, the one or more back fasteners 44 may be joined to the back portion 24, the back ears 25 or both and the one or more front fasteners 45 may be joined to the front portion 22, the front ears 23, or both. The one or more back fasteners 44 may be one or more discrete pieces of material joined to the diaper 10 and adapted to align with and work in conjunction with the one or more front fasteners 45, which may be one or more discrete pieces of material joined to the diaper 10. For example, the front fastener 45 may be a piece of loop material joined with the outercover 32 in the front portion 22 and configured to engage hook-type back fasteners 44 when the diaper 10 is wrapped about the waist and legs of a user.

Alternatively, the one or more front fasteners 45 may include portions of the outercover 32, the bodyside liner 30, or both and be configured to engage hook-type back fasteners 44. For example, the outercover 32 may be configured to be a non-woven material suitable for engagement with hook materials. In such an embodiment, hook-type fasteners 44 may be located at the back ear 25 and wrapped around the waist of the wearer. The hook-type fasteners 44 may then be engaged directly with the nonwoven outercover 32 to join the back portion 24 with the front portion 22 and secure the diaper 10 about the waist of the wearer.

Alternatively, the one or more front fasteners 45 may include hook-type fasteners and the one or more back fasteners 44 may include one or more complementary loop-type fasteners. In various embodiments, the one or more back fasteners 44 and the one or more front fasteners 45 may comprise any suitable materials adapted to join the back portion 24 to the front portion 22 of the diaper 10 thus securing the diaper about the waist of a wearer. Suitable fastening materials include hook and loop materials, adhesives, adhesive tapes, cohesives, snaps, buttons, latches, hooks, and the like, and combinations thereof. In some embodiments both the front portion 22 and the back portion 24 may include dual fasteners as is known in the art.

The absorbent core 34 is positioned between the bodyside liner 30 and the outer cover 32 to form the diaper 10. The absorbent core 34 is generally conformable and capable of absorbing and retaining body exudates. The absorbent core 34 may include superabsorbent material, staple fibers, binder fibers, and the like, and combinations thereof as is known in the art. The absorbent core 34 may have any of a number of shapes and sizes. For example, the composite absorbent core may be rectangular, I-shaped or T-shaped. The size and absorbent capacity of the absorbent core 34 should be compatible with the size of the intended wearer and the fluid loading imparted by the intended use of the diaper.

In various embodiments, the surge portion 33 serves to quickly collect and temporarily hold discharged fluids and then to eventually release the fluids into the absorbent core 34. Various woven and nonwoven materials can be used to construct the surge portion 33. For example, the surge portion 33 may be a layer of a spunbonded or meltblown web of polyolefin fibers. The surge portion 33 may also be a bonded carded web of natural and synthetic fibers. The surge portion 33 may be a substantially hydrophobic material and, optionally, can be treated with a surfactant or otherwise to impart a desired level of wettability and hydrophilicity.

Containment flaps 52 may be connected to the bodyside liner or other components as is well known in the art. Suitable configurations of the containment flaps 52 are described, for example, in U.S. Pat. No. 5,599,338 issued Feb. 4, 1997, to K. Enloe, the entirety of which is incorporated herein by reference where not contradictory.

The umbilical feature 58 includes at least one line of weakness 60 located in the front portion 22, at least one umbilical cover 64 and at least one umbilical cover anchor 66. The at least one line of weakness 60 is adapted to be torn by a caregiver if the caregiver opts to do so. The at least one umbilical cover 64 is defined in part by the at least one line of weakness 60. The at least one umbilical cover 64 has a starting position and an anchored position. The at least one umbilical cover 64 is moveable from the starting position to the anchored position upon tearing of the at least one line of weakness 60. In various embodiments, the umbilical feature 58 may also include at least one fold line 62, at least one folding guide 70 and/or at least one line of weakness indicator 72.

As used herein, the term "umbilical feature" refers to a system adapted to minimize contact with the umbilical area of a baby. The present invention provides an option to the caregiver in that the caregiver may choose to use the diaper as provided or the caregiver may choose to create an umbilical relief area proximate the baby's umbilical cord and/or navel utilizing the umbilical feature described herein. If the caregiver chooses to utilize the umbilical feature, the diaper is torn along the line of weakness in the front portion of the diaper. The umbilical cover is moved from the starting position to an anchored position and is secured in the anchored position by at least one umbilical cover anchor thus creating and maintaining the umbilical relief area. The umbilical relief area, when created, is adapted to avoid or minimize contact between the diaper and the umbilical cord and/or navel of the baby wearing the diaper. If the caregiver chooses not to use the umbilical feature, the at least one line of weakness is left intact, the at least one umbilical cover is left in the starting position and the diaper is used in a conventional way.

The lines of weakness 60 are located in the front portion 22 of the diaper 10. The lines of weakness 60 may be located proximate the front waist edge 48 and/or the lines of weakness 60 may be remote from the front waist edge 48. In various embodiments, one or more line of weakness 60 may be integral with the front waist edge 48 and one or more line of weakness 60 may be remote from the front waist edge 48. In various embodiments, the diaper 10 may include 1, 2, 3, 4, or more than 4 lines of weakness 60. The lines of weakness 60 may have a length from 1 mm to 60 mm. In some embodiments, the lines of weakness 60 may have a length from 20 mm to 50 mm or from 30 mm to 45 mm.

The lines of weakness 60 may be created by perforating the diaper 10 in the front portion 22. The lines of weakness 60 may be created by partial pressure cutting, partial ultrasonic cutting, partial thermal deformation, mechanical thinning or other processes as are known in the art. Regardless of the method of creation, the lines of weakness 60 may extend, at least partially, through the liner 30, the front waist elastic 40, the outercover 32, the one or more front fasteners 45, the absorbent core 34, or combinations thereof. In some embodiments, the lines of weakness 60 may be formed by perforating the outercover 32, the front waist elastic 40, and the liner 30 in the front portion 22 between the one or more front fasteners 45 and the front waist edge 48. As used herein "perforating" means to make one or more holes, slits, apertures, voids, or the like, or combinations thereof through one or more materials to facilitate separation. The perforations may include a line of holes defining a perforated area wherein the holes are separated by intact material or materials defining an intact area. The amount of perforated area relative to the intact area can be altered to change the amount of force required to tear the diaper 10 along the line of weakness 60.

Figure 8:
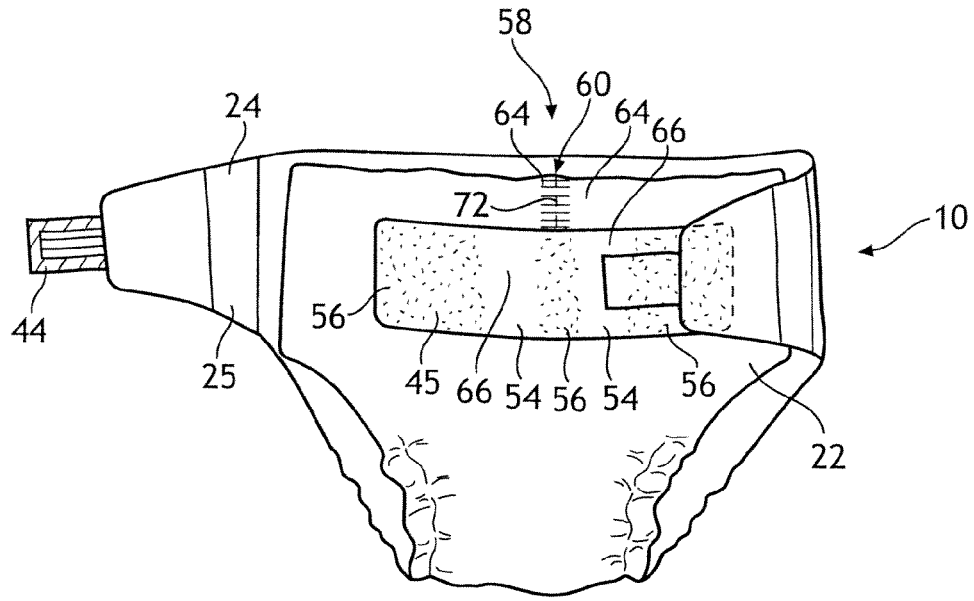
FIG. 8 representatively illustrates a front perspective view of a partially fastened absorbent article with the umbilical feature in the closed condition.

The lines of weakness 60 may be made more visible or prominent through the use of one or more line of weakness indicators 72 as illustrated in FIG. 8. The line of weakness indicators 72 may include printing, embossing, bonding, or the like, or combinations thereof of one or more indicia proximate the lines of weakness 60. The lines of weakness indicators 72 are adapted to draw the caregiver's attention to the lines of weakness 60 and may include shapes, symbols, text, graphics, or the like, or combinations thereof.

The lines of weakness 60 are preferably, though not necessarily, sufficiently strong to maintain the umbilical feature 58 in the closed condition during use if so desired by the caregiver. The lines of weakness 60 can be torn upon application of force, for example manual force provided by a caregiver, allowing the at least one umbilical cover 64 to be moved from the starting position to the anchored position thereby transitioning the umbilical feature 58 from a closed condition to an open condition. When in the open condition, the umbilical feature 58 defines an umbilical relief area 68. As used herein, the term "closed condition" describes the umbilical feature 58 when the at least one umbilical cover 64 is in the starting position and the at least one line of weakness 60 is intact. As used herein, the term "open condition" describes the umbilical feature 58 when the at least one line of weakness 60 has been torn and the at least one umbilical cover 64 is in the anchored position.

Figure 16:
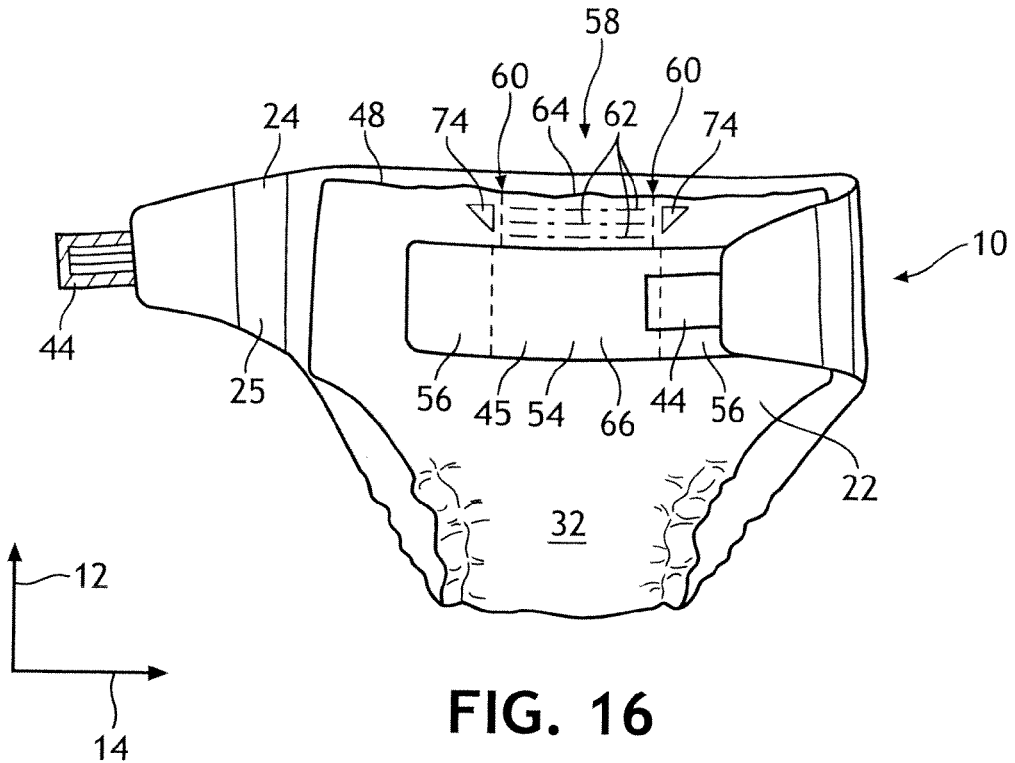
FIG. 16 representatively illustrates a front perspective view of a partially fastened absorbent article with the umbilical feature in the closed condition.

In some embodiments, the umbilical feature 58 may include one or more fold lines 62 as illustrated in FIGS. 2, 4, 16 and 18. The fold lines 62 may be created by ultrasonic bonding, pressure bonding, thermal bonding, or other processes by which a crease, crimp, hinge or the like is formed, or combinations thereof. The fold lines 62 are adapted to allow the umbilical cover 64 to fold in the proper direction to create the umbilical relief area 68. The fold lines 62 may also be adapted to make the umbilical covers 64 "floppy" in that there is minimal force resisting the movement of the umbilical covers 64 from the starting position to the anchored position. In some embodiments, the umbilical feature 58 may include multiple fold lines adapted to enable a caregiver to customize the size and/or shape of the umbilical relief area 68 as illustrated in FIG. 16.

Figure 4:
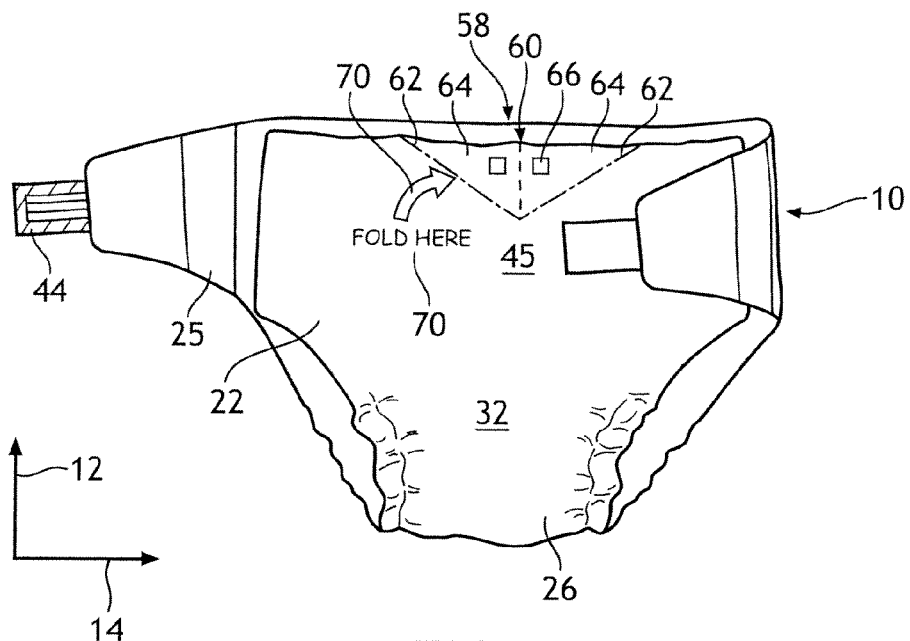
FIG. 4 representatively illustrates a front perspective view of a partially fastened absorbent article with the umbilical feature in the closed condition.
Figure 5:
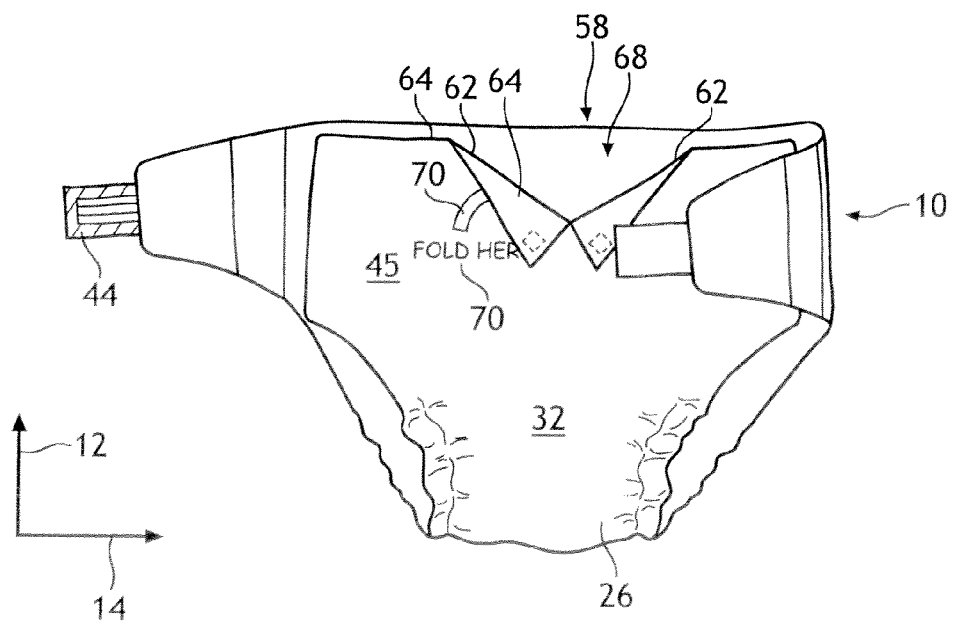
FIG. 5 representatively illustrates a front perspective view of the absorbent article of FIG. 4 with the umbilical feature in the opened condition.

In some embodiments, the umbilical feature 58 may further include one or more folding guides 70 as illustrated in FIGS. 4 and 5. The folding guides 70 are adapted to assist the caregiver in locating the fold lines 62 and/or selecting the proper fold line 62 to utilize. The folding guides 70 may include printing, embossing, bonding, or the like and combinations thereof. The folding guides 70 may include text, figures, graphics, arrows, symbols, and the like and combinations thereof.

The umbilical relief area 68 is defined by the umbilical feature 58 when in the open condition and may be configured in various sizes and shapes depending on the various sizes and shapes of the umbilical covers 64. The sizes and shapes of the umbilical covers 64 are dictated in part by the shape, size, and location of the lines of weakness 60 and/or the fold lines 62. For example, a line of weakness 60 located generally in the longitudinal direction 12 and extending from the front waist edge 48 towards the crotch portion 26 will result in triangular-shaped umbilical covers 64 upon tearing the line of weakness 60. In another example, two lines of weakness 60 may be located generally in the longitudinal direction 12 and spaced apart from one another in the lateral direction 14. Upon tearing the lines of weakness 60 a rectangular-shaped umbilical cover 64 will be formed. In yet another example, two lines of weakness 60 may intersect one another at essentially right angles forming a T-shape or X-shape which will result in the formation of triangular-shaped umbilical covers 64 upon tearing the lines of weakness 60.

The umbilical cover anchors 66 may be configured in various sizes, shapes, quantities and materials in various embodiments. In some embodiments, the umbilical cover anchors 66 may be pockets formed by bonding portions of the one or more front fasteners 45 or front waist elastic 40 and leaving at least one portion unbonded. The unbonded portion or portions are located between bonded portions and define one or more pockets. Alternatively, the umbilical cover anchors 66 may be pockets formed by joining one or more discrete pieces of material to the liner 30, outercover 32, one or more front fasteners 45, one or more back fasteners 44, front waist elastic 40, or combinations thereof.

In embodiments utilizing pockets as the umbilical cover anchors 66, the umbilical covers 64 are adapted to be tucked, at least partially, into the pockets by the caregiver to maintain the umbilical covers 64 in the anchored position and the umbilical feature 58 in the open condition. The umbilical covers 64 are adapted to be tucked by locating the at least one line of weakness 60 proximate the pocket or pockets. This allows the at least one line of weakness 60 to be torn and the umbilical covers 64 to be moved and the moveable covers 64 to be directed towards the one or more pockets and tucked therein. The shape of the umbilical covers 64 and the shape and size of the pocket may also be adapted to work in conjunction with one another. For example, a line of weakness 60 may be located generally in the longitudinal direction 12 and extend from the front waist edge 48 towards the crotch portion 26. One corner of the resulting triangular-shaped umbilical covers 64 may be suitably tucked into a relatively small pocket. Alternatively, two lines of weakness 60 may be located generally in the longitudinal direction 12 and spaced apart in the lateral direction 14 resulting in a rectangular-shaped umbilical cover 64 when the lines of weakness 60 are torn. This type of umbilical cover 64 may be tucked into a larger pocket to maintain the umbilical cover 64 in the anchored position.

In some embodiments, the umbilical cover anchors 66 may be one or more discrete pieces of material permanently joined to the bodyside liner 30, outercover 32, one or more front fasteners 45, one or more back fasteners 44, front ears 23, back ears 25, front waist elastic 40 or combinations thereof. Materials suitable for use as umbilical cover anchors 66 include, but are not limited to, hook, loop, adhesive, cohesive, buttons, snaps, or the like, or combinations thereof. In these embodiments, the umbilical feature 58 can be maintained in the open condition by anchoring the umbilical cover 64 in the anchored position by means of the umbilical cover anchors 66.

For example, the umbilical cover anchors 66 may be permanently joined to the umbilical cover 64 when the umbilical cover 64 is in the starting position, i.e., the umbilical feature 58 is in the closed condition. In these embodiments, the diaper 10 may be torn along the at least one line of weakness 60 and the umbilical cover 64 may be moved, along with the umbilical cover anchor 66, from the starting position to the anchored position thereby creating the umbilical relief area 68. The umbilical cover 64 may be joined via the umbilical cover anchor 66 to the one or more front fasteners 45, liner 30, front waist elastic 40, or other suitable diaper components to maintain the umbilical feature 58 in the open condition.

Alternatively, the umbilical cover anchors 66 may be permanently joined to the one or more front fasteners 45, liner 30, front waist elastic 40, outer cover 32 or other suitable diaper component or components when the umbilical cover 64 is in the starting position, i.e., the umbilical feature 58 is in the closed condition. In these embodiments, the diaper 10 may be torn along the at least one line of weakness 60 wherein the umbilical cover 64 may be moved, without the umbilical cover anchors 66, from the starting position to the anchored position thereby creating the umbilical relief area 68. The umbilical cover 64 may be joined via the umbilical cover anchor 66 to maintain the umbilical feature 58 in the open condition.

Figure 2:
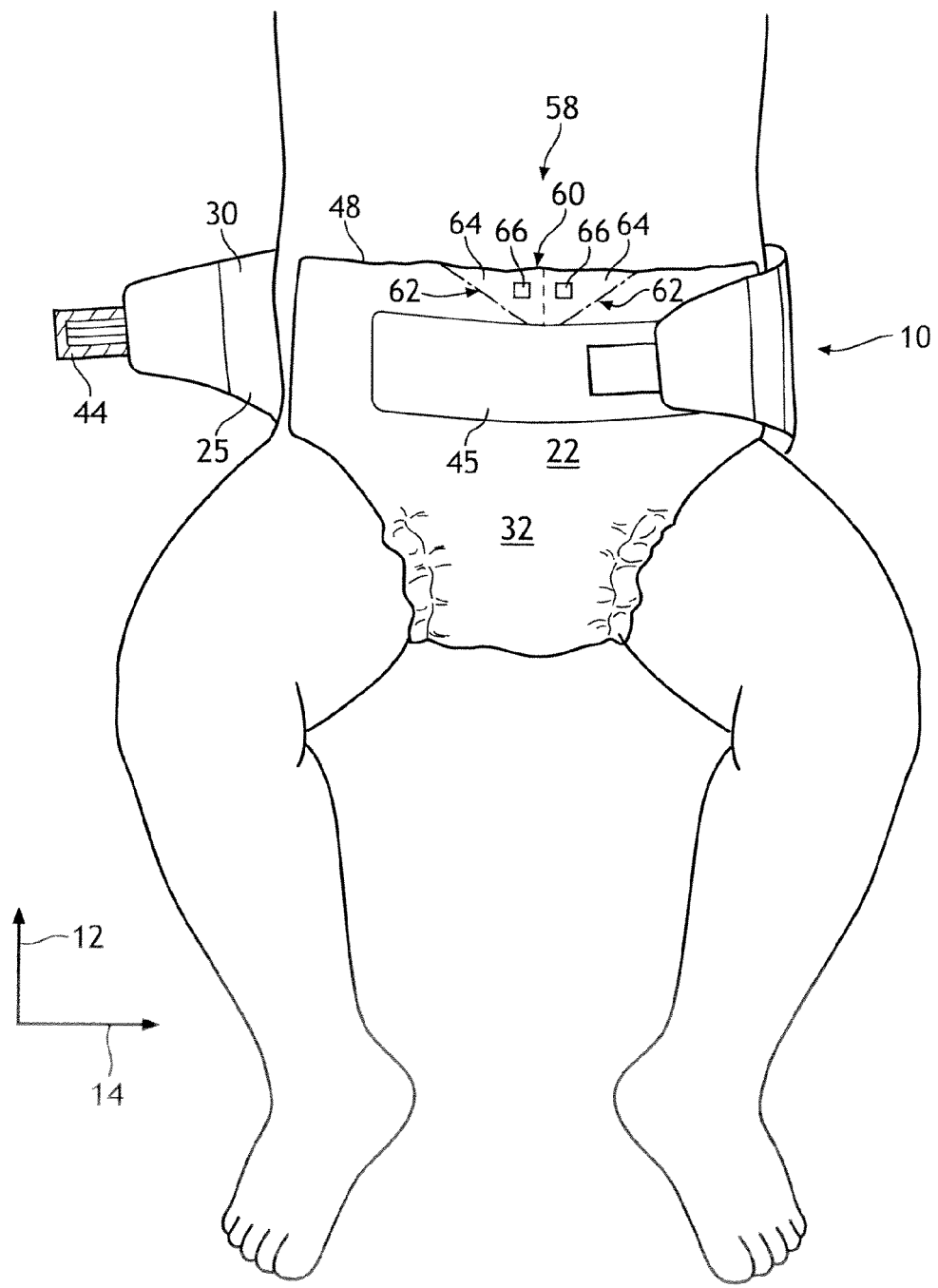
FIG. 2 representatively illustrates a front perspective view of a partially fastened absorbent article about the waist and legs of a wearer.

Referring now to FIG. 2, a diaper 10 is shown in a partially fastened condition on a baby. The back fasteners 44 are joined to the back ears 25 in the back portion 24. The back ears 25 are wrapped around the baby's waist and hips and joined with the front fastener 45 located in the front portion 22 to maintain the diaper generally in the position shown. The diaper 10 includes an umbilical feature 58 that includes a line of weakness 60, two umbilical cover anchors 66, two umbilical covers 64, and two fold lines 62. The fold lines 62 are depicted as dot-dash lines. The line of weakness 60 is depicted as a dotted line.

In the embodiment illustrated in FIG. 2, the umbilical feature 58 is illustrated in the closed condition, the umbilical covers 64 are in the starting position and one of the umbilical cover anchors 66 is permanently joined to each of the two umbilical covers 64. The line of weakness 60 generally extends in the longitudinal direction 12 from the front waist edge 48 to the front fastener 45. The line of weakness 60 is located at approximately the center of the diaper 10 in the lateral direction 14. The line of weakness 60 extends, at least partially through the liner 30 and the outercover 32. In various embodiments, the diaper 10 may optionally include a front waist elastic 40 joined in the front portion 22 proximate the front waist edge 48. In such embodiments, the line of weakness 60 may extend, at least partially through the front waist elastic 40 to facilitate tearing.

Figure 3:
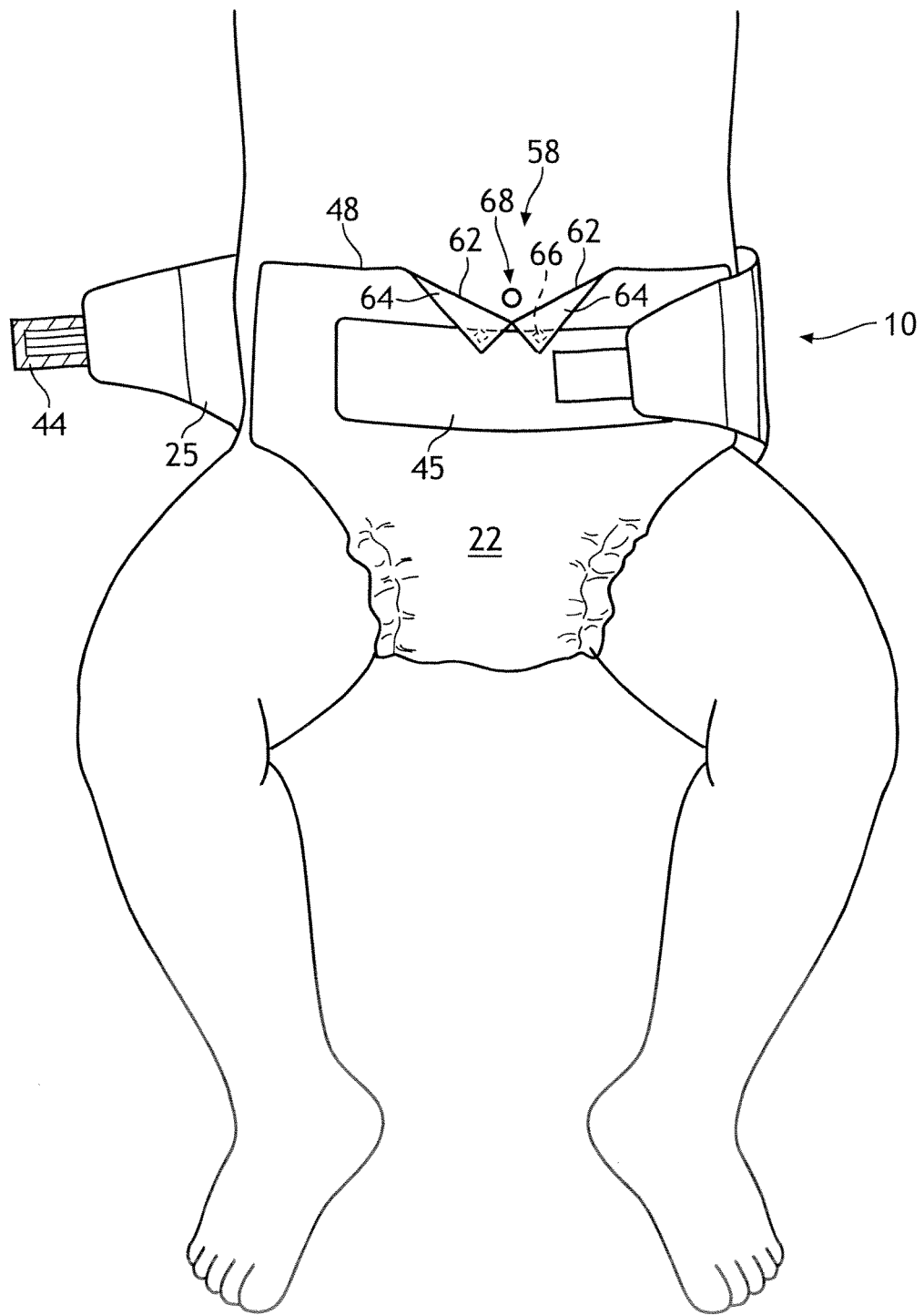
FIG. 3 representatively illustrates a front perspective view of the absorbent article of FIG. 2 partially fastened about the waist and legs of a wearer with the umbilical feature in the opened condition.

Referring now to FIG. 3, the diaper 10 of FIG. 2 is shown in a partially fastened condition on a baby with the umbilical feature 58 in the opened condition and the umbilical covers 64 in the anchored position. The two umbilical covers 64 are defined in part by the line of weakness 60 and are moveable from the starting position to the anchored position upon tearing the diaper 10 along the line of weakness 60 and folding the umbilical covers 64 along the fold lines 62. Each umbilical cover 64 includes one umbilical cover anchor 66. The umbilical cover anchors 66 are adapted to join with the front fastener 45 to maintain the umbilical feature 58 in the open condition thereby creating an umbilical relief area 68 in the front portion 22.

In FIG. 3, the umbilical feature 58 is illustrated in the open condition. A caregiver, desiring to utilize the umbilical feature 58 of the diaper 10 of FIG. 2, may tear the line of weakness 60 from the front waist edge 48 to the front fastener 45. Tearing the line of weakness 60 allows the two triangular-shaped umbilical covers 64 to be moved from the starting position to the anchored position. The movement of the umbilical covers can occur along the fold lines 62. The fold lines 62 extend from a position along the front waist edge 48 remote from the line of weakness 60. The fold lines 62 are located at approximately 45 degrees relative to the front waist edge 48.

The two umbilical cover anchors 66 are permanently joined to the two umbilical covers 64 proximate the front waist edge 48 and proximate the line of weakness 60. Upon tearing the line of weakness 60, the umbilical covers 64 may be moved and the anchors 66 may be engaged with the front fastener 45, as illustrated in FIG. 3, to maintain the umbilical feature 58 in the open condition. Alternatively, the umbilical cover anchors 66 may be joined with the outercover 32, the back fastener 44, the front fastener 45, or combinations thereof.

As used herein, the term "defined in part by the line of weakness" refers to the fact that the umbilical cover or covers have at least one edge that results from tearing the one or more line of weakness. Said another way, after the one or more lines of weakness are torn, the one or more umbilical covers have one or more edges that were formerly adjacent the one or more lines of weakness.

Referring now to FIG. 4, a diaper 10 is shown in a partially fastened condition. The back fasteners 44 are joined to the back ears 25 in the back portion 24. The back ears 25 are wrapped around and joined with the front fasteners 45 located in the front portion 22 to maintain the diaper generally in the position shown. In this embodiment, the outer cover 32 is adapted to function as the front fastener 45 and may, for example, be the loop portion of a hook and loop fastening system as is known in the art. The diaper 10 includes an umbilical feature 58 that includes one line of weakness 60, two umbilical covers 64, two umbilical cover anchors 66, two fold lines 62 and two folding guides 70. The fold lines 62 are illustrated as dot-dash lines.

In the embodiment illustrated in FIG. 4, the folding guides 70 include a graphic arrow and the text "Fold Here". The folding guides 70 are adapted to draw the caregiver's attention to the location of the fold lines 62. The umbilical feature 58 is illustrated in the closed condition and the umbilical covers 64 are illustrated in the starting position. The line of weakness 60 generally extends in the longitudinal direction 12 from the front waist edge 48 towards the crotch portion 26 and is located at approximately the center of the diaper 10 in the lateral direction 14. The line of weakness 60 may extend in the longitudinal direction 12 as far as desired, but preferably will stop prior to reaching the absorbent core. The line of weakness 60 extends, at least partially through the liner 30 and the outercover 32 to facilitate tearing if desired. The umbilical cover anchors 66 are permanently joined with the umbilical covers 64 near the corner of the umbilical covers 64 defined by the line of weakness 60 and the front waist edge 48.

Referring now to FIG. 5, the diaper 10 of FIG. 4 is shown in a partially fastened condition with the umbilical feature 58 in the opened condition and the umbilical covers 64 in the anchored position. In this embodiment, the umbilical feature 58 includes two umbilical covers 64 defined in part by the line of weakness 60. The umbilical covers 64 are moveable from the starting position to the anchored position upon tearing the diaper 10 along the line of weakness 60 and by folding the umbilical covers 64 along the fold lines 62. Each umbilical cover 64 includes one umbilical cover anchor 66. The umbilical cover anchors 66 are adapted to join with the front fastener 45, which in this embodiment is the outer cover 32, to maintain the umbilical feature 58 in the open condition in the front portion 22 thereby defining an umbilical relief area 68.

In FIG. 5, the umbilical feature 58 is illustrated in the open condition. A caregiver, desiring to utilize the umbilical feature 58 of the diaper 10 of FIG. 4, may tear the line of weakness 60 thereby allowing the two triangular-shaped umbilical covers 64 to be moved from the starting position to the anchored position. The movement of the umbilical covers can occur along the fold lines 62. The fold lines 62 extend from a position along the front waist edge 48 outboard from the line of weakness 60 to the end of the line of weakness 60 that is closest to the crotch portion 26. The fold lines 62 are highlighted to the caregiver by means of the folding guides 70. The two umbilical cover anchors 66 are joined with the two umbilical covers 64 proximate the front waist edge 48 and proximate the line of weakness 60. Upon tearing the line of weakness 60, moving the umbilical covers 64 along the fold lines 62, the umbilical feature 58 may be secured in the anchored position by joining the umbilical cover anchors 66 with the front fastener 45.

As illustrated In FIG. 5, the back fasteners 44 may at least partially engage the inner surface of the umbilical cover 64 thus maintaining the umbilical cover 64 within the union of the back fasteners 44 and the front fastener 45. However, neither the one or more back fasteners 44, nor the one or more front fasteners 45 nor the union of the front and back fasteners are considered the umbilical cover anchor 66.

Figure 6:
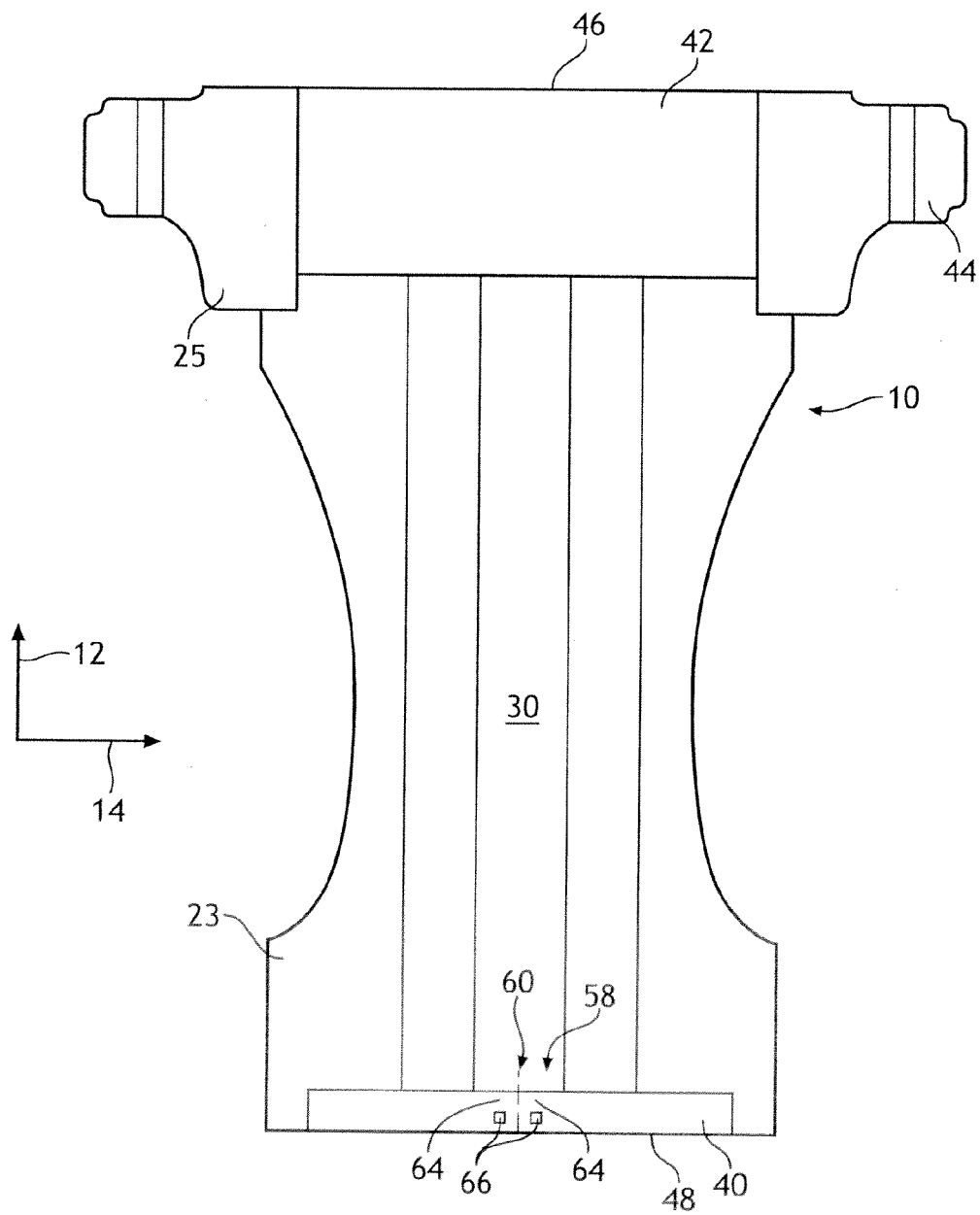
FIG. 6 representatively illustrates a top plan view of an absorbent article in a stretched and laid flat condition with the surface of the article that contacts the skin of the wearer facing the viewer and with the umbilical feature in the closed condition.

Referring now to FIG. 6, a diaper 10 is shown in an unfastened condition with the body facing surface facing the viewer. The diaper 10 includes an umbilical feature 58, illustrated in the closed condition, which includes one line of weakness 60, two umbilical cover anchors 66 and two umbilical covers 64. The two umbilical cover anchors 66 are permanently joined with the umbilical covers 64 when the umbilical covers 64 are in the starting position. The two umbilical cover anchors 66 are located on the front waist elastic 40 in this embodiment. The line of weakness 60 extends, at least partially, through the outer cover 32, the bodyside liner 30 and the front waist elastic 40 to facilitate tearing.

Figure 7:
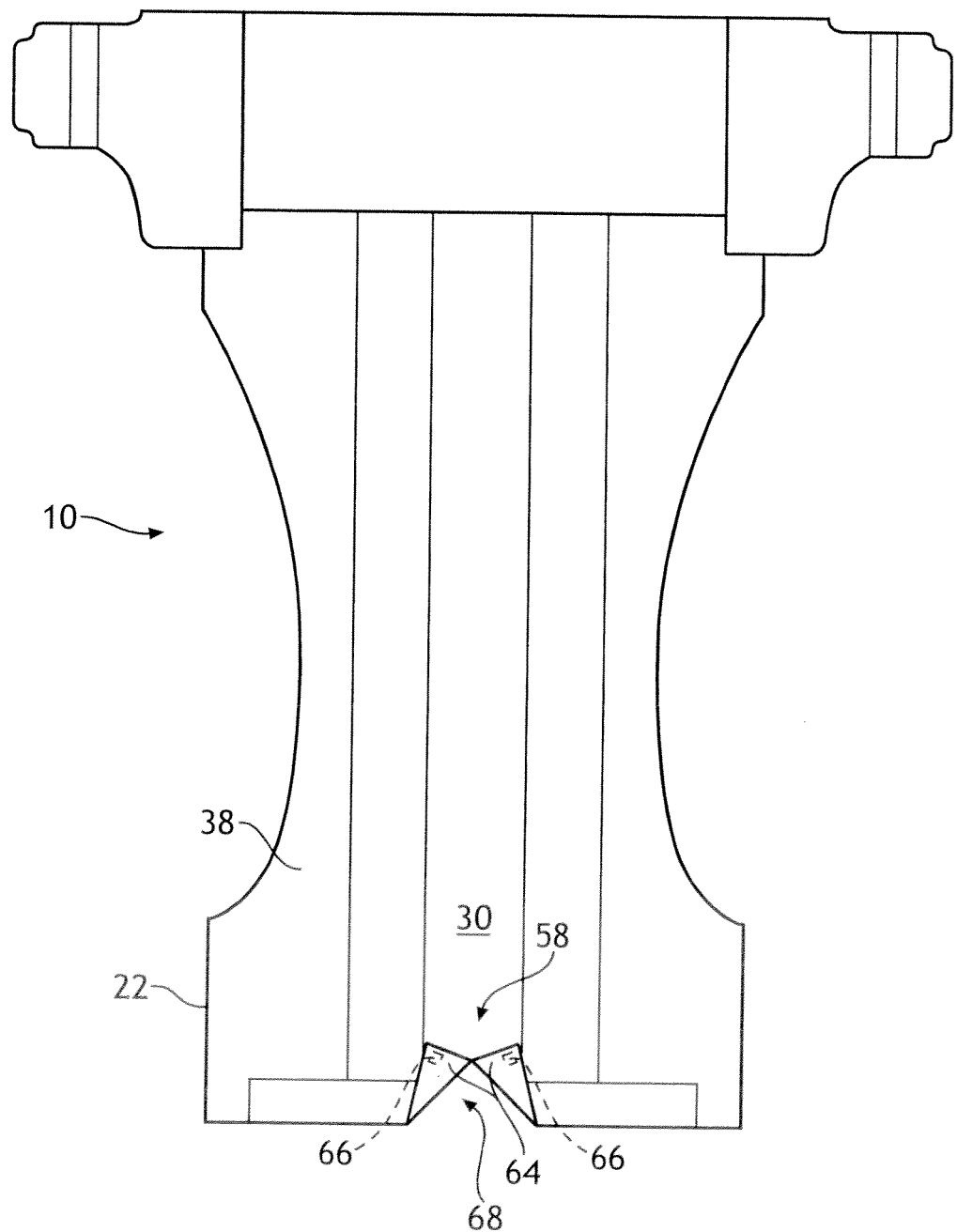
FIG. 7 representatively illustrates a top plan view of the absorbent article of FIG. 6 with the umbilical feature in the opened condition.

Referring now to FIG. 7, the diaper 10 of FIG. 6 is shown in an unfastened condition with the body facing surface facing the viewer. The umbilical feature 58 is illustrated in the opened condition and the umbilical covers 64 in the anchored position. The umbilical cover anchors 64 are adapted to join with the bodyside liner 30 to hold the umbilical covers 64 in the anchored position and the umbilical feature 58 in the open condition thereby creating an umbilical relief area 68. In various embodiments, the diaper 10 may include body adhesive in the front portion 22 to at least partially adhere the diaper 10 to the body of the baby. In such embodiments, the body adhesive may also join the umbilical covers 64 with the body facing surface to hold the umbilical covers 64 in the anchored position.

Referring now to FIG. 8, a diaper 10 is shown in a partially fastened condition. The back fasteners 44 are joined to the back ears 25 in the back portion 24. The back ears 25 are wrapped around and joined with the front fastener 45 located in the front portion 22 to maintain the diaper generally in the position shown. The diaper 10 also includes an umbilical feature 58 that includes one line of weakness 60, two umbilical cover anchors 66, two umbilical covers 64, and a line of weakness indicator 72. The line of weakness indicator 72 is illustrated as a column of horizontal lines.

In this embodiment, the two umbilical cover anchors 66 are pockets formed in part by the front fastener 45. The front fastener 45 may be joined to the outer cover 32 in the front portion 22 at laterally spaced bonded portions 56. The bonded portions 56 may include adhesive, ultrasonic bonding, thermal bonding, pressure bonding, and the like and combinations thereof. In this embodiment, unbonded portions 54 are located between the bonded portions 56 of the front fastener 45, creating pockets that may be utilized as umbilical cover anchors 66. The pockets are sized to receive at least a portion of the umbilical covers 64. The umbilical feature 58 is illustrated in the closed condition and the umbilical covers 64 are illustrated in the starting position. A suitable method of partially bonding the front fastener 45 to the outer cover 32 is described in U.S. Pat. No. 5,318,555 issued Jun. 7, 1994 to Siebers et al. the entirety of which is incorporated herein by reference where not contradictory.

Figure 9:
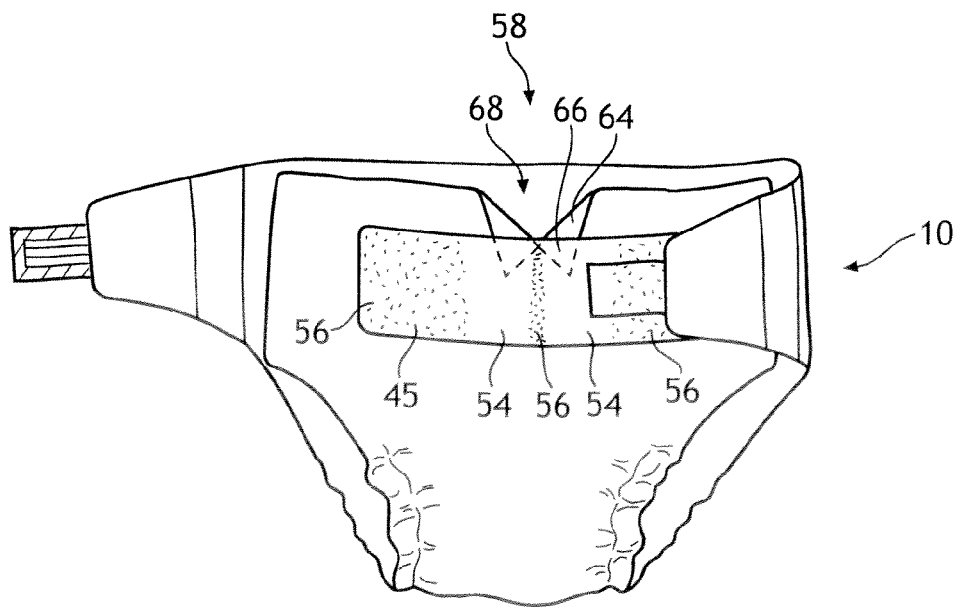
FIG. 9 representatively illustrates a front perspective view of the absorbent article of FIG. 8 with the umbilical feature in the opened condition.

Referring now to FIG. 9, the diaper 10 of FIG. 8 is shown in a partially fastened condition with the umbilical feature 58 in the opened condition and the umbilical covers 64 in the anchored position. In this embodiment, the umbilical feature 58 includes two umbilical covers 64 defined in part by the line of weakness 60. The umbilical covers 64 are moveable from the starting position to the anchored position upon tearing the line of weakness 60. In this embodiment, the umbilical cover anchors 66 are pockets defined by the unbonded portions 54 located between the front fastener 45 and the outer cover 32 and between the bonded portions 56. The pockets are adapted to receive the umbilical covers 64, anchor the umbilical covers 64 in the anchored position and to maintain the umbilical feature 58 in the open condition thereby defining an umbilical relief area 68. As illustrated, the two unbonded portions 54 are located between the three bonded portions 56. The unbonded portions 54 are sized to receive a portion of the umbilical covers 64.

In this embodiment, a caregiver wishing to utilize the umbilical feature 58 of the diaper 10 of FIG. 8 may locate the line of weakness 60 using the line of weakness indicator 72. The caregiver may then tear along the line of weakness 60. The umbilical covers 64 may then be moved from the starting position to the anchored position. The user may maintain the umbilical covers 64 in the anchored position by tucking at least a portion of the umbilical covers 64 between the front fastener 45 and the outer cover 32 in the unbonded portions 54. The umbilical feature 58, in the open condition in the front portion 22, defines an umbilical relief area 68.

Figure 10A:
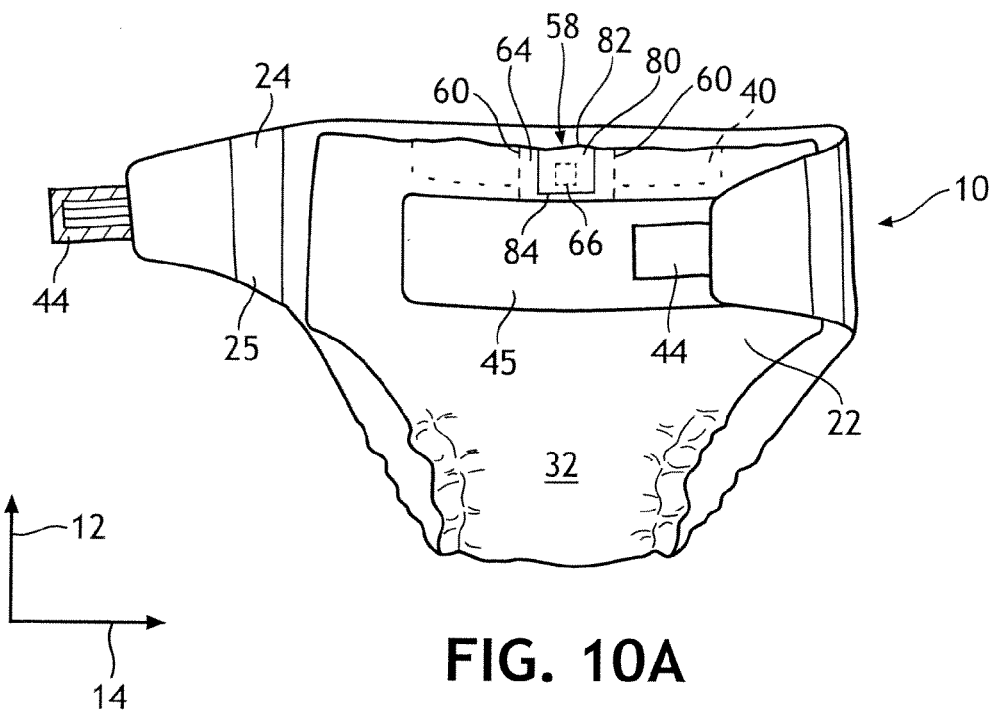
FIG. 10A representatively illustrates a front perspective view of a partially fastened absorbent article with the umbilical feature in the closed condition.
Figure 10B:
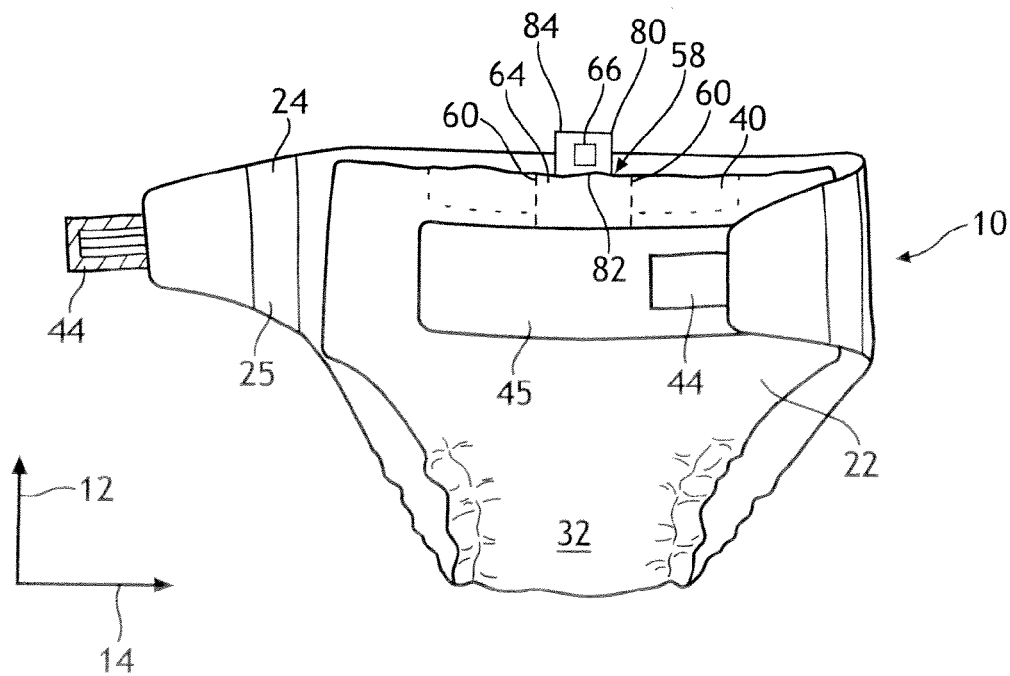
FIG. 10B representatively illustrates a front perspective view of a partially fastened absorbent article with the umbilical feature in the closed condition.

Referring now to FIGS. 10A and 10B, a diaper 10 is shown in a partially fastened condition. The back fasteners 44 are joined to the back ears 25 in the back portion 24. The back ears 25 are wrapped around and joined with the front fastener 45 located in the front portion 22 to maintain the diaper generally in the position shown. The diaper 10 includes an umbilical feature 58 that includes two lines of weakness 60, one umbilical cover 64, an umbilical cover anchor 66 and an umbilical cover tab 80. The umbilical feature 58 is illustrated in the closed condition and the umbilical cover 64 is illustrated in the starting position. The lines of weakness 60 extend from the front waist edge 48 to the front fastener 45. The lines of weakness 60 extend, at least partially, through the outer-cover 32, the bodyside liner 30, and the front waist elastic 40.

The umbilical cover tab 80 has a closed position and an extended position. The umbilical cover tab 80 is illustrated in the closed position in FIG. 10A and the umbilical cover tab 80 is illustrated in the extended position in FIG. 10B. The umbilical cover tab 80 has an attached end 82 and a grasping end 84. The umbilical cover tab 80 covers the umbilical cover anchor 66 when the umbilical cover tab 80 is in the closed position. The umbilical cover anchor 66 may be permanently joined to the outer cover 32 or the front fastener 45 or to a separate piece of material which in turn is permanently joined to the outer cover 32 or the front fastener 45. In these embodiments, the umbilical cover anchor 66 may be releasably joined to the umbilical cover tab 80. Alternatively, the umbilical cover anchor 66 may be permanently joined to the umbilical cover tab 80 as illustrated in FIG. 10B. The umbilical cover tab 80 may be joined by any suitable means. For example, the umbilical cover tab 80 may be joined with adhesive, heat, ultrasonics, and the like, and combinations thereof.

The umbilical cover anchor 66 may desirably be covered by the umbilical cover tab 80 when the umbilical feature 58 is in the closed condition. This minimizes contact between the umbilical cover anchor 66 and the caregiver, the baby's skin, the baby's clothes, and other surfaces that may be irritated or snagged if contacted by the umbilical cover anchor 66. If the caregiver desires to utilize the umbilical feature 58, the umbilical cover tab 80 is grasped at the grasping end 84 and the umbilical cover tab 80 is moved from the closed position of FIG. 10A to the extended position of FIG. 10B thereby exposing the umbilical anchor 66. The caregiver may then pull on the umbilical cover tab 80 thereby tearing the front portion 22 of the diaper 10 along the lines of weakness 60. Tearing along the lines of weakness 60 allows the umbilical cover 64 to be moved from the starting position.

Figure 11:
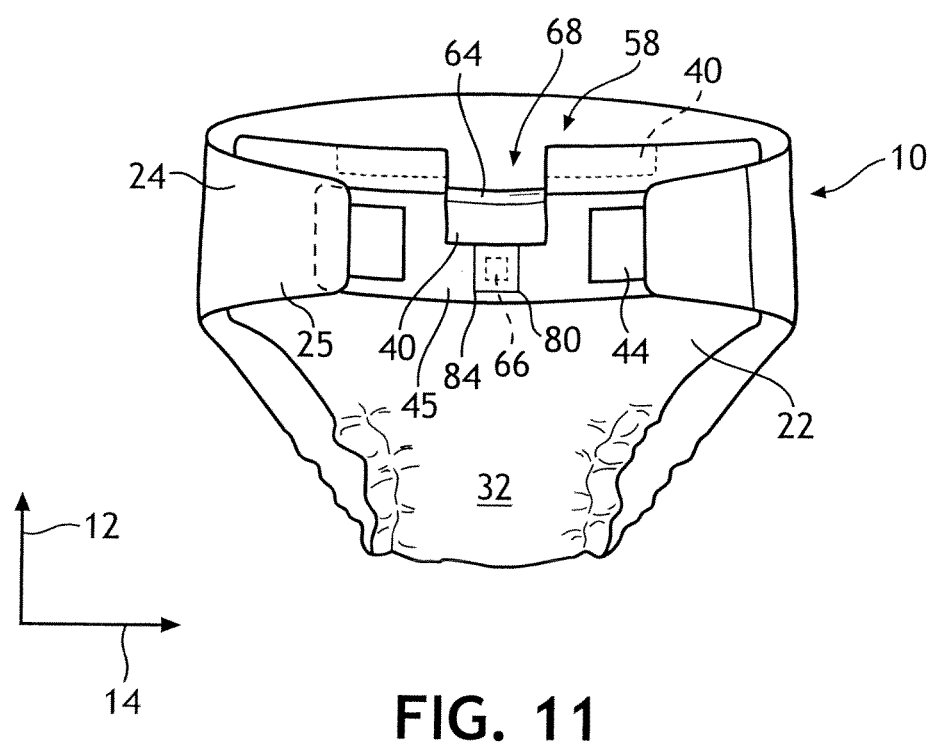
FIG. 11 representatively illustrates a front perspective view of the absorbent article of FIGS. 10A and 10B with the umbilical feature in the opened condition.

Referring now to FIG. 11, the diaper 10 of FIGS. 10A and 10B is shown in a fastened condition with the umbilical feature 58 in the opened condition and the umbilical cover 64 in the anchored position. The umbilical feature 58 includes the umbilical cover 64 which is defined, in part, by the lines of weakness 60. The umbilical cover 64 is moveable from the starting position to the anchored position. The umbilical cover anchor 66 is joined with the front fastener 45 to maintain the umbilical cover 64 in the anchored position and the umbilical feature 58 in the open condition. The umbilical cover anchor 66 also maintains the umbilical cover tab 80 in the extended position. The umbilical feature 58, in the open position, in the front portion 22, defines an umbilical relief area 68.

Figure 12:
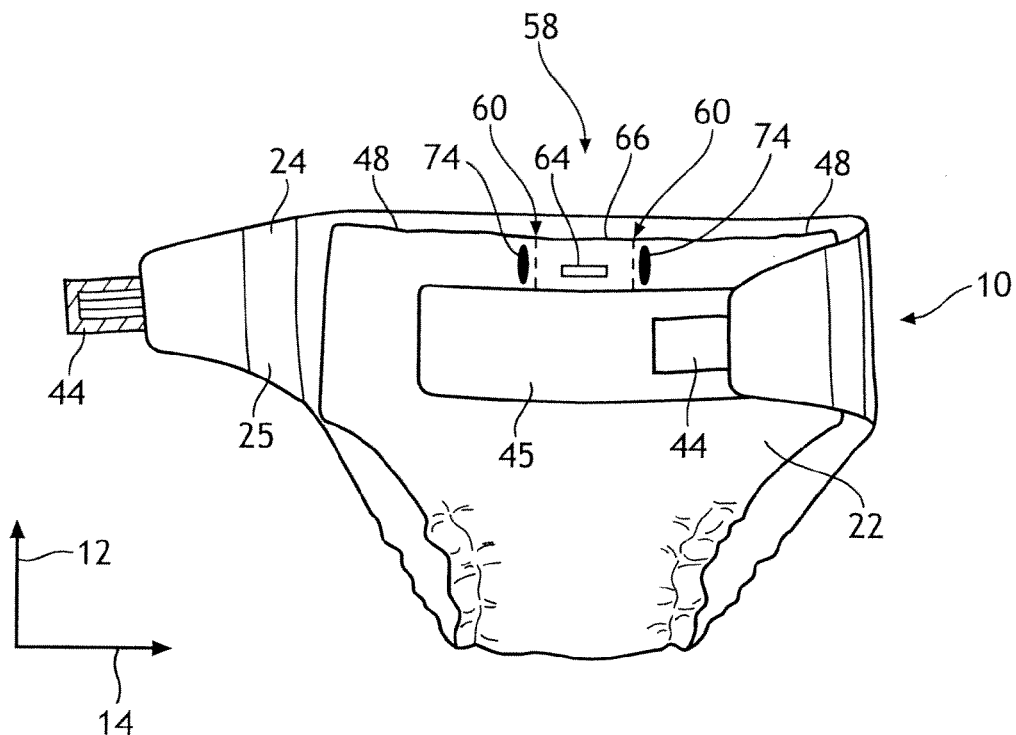
FIG. 12 representatively illustrates a front perspective view of a partially fastened absorbent article with the umbilical feature in the closed condition.

Referring now to FIG. 12, a diaper 10 is shown in a partially fastened condition. The back fasteners 44 are joined to the back ears 25 in the back portion 24. The back ears 25 are wrapped around and joined with the front fastener 45 located in the front portion 22 to maintain the diaper generally in the position shown. The diaper 10 also includes an umbilical feature 58 that includes two lines of weakness 60, one umbilical cover 64 and one umbilical cover anchor 66. The umbilical feature 58 is illustrated in the closed condition and the umbilical cover 64 is illustrated in the starting position.

The two lines of weakness 60 extend generally in the longitudinal direction 12 from the front waist edge 48 to the front fastener 45. The two lines of weakness 60 are spaced apart from about 20 mm to 50 mm. The umbilical cover anchor 66 is generally centered in the lateral direction 14 between the two lines of weakness 60 and may be located anywhere between the front waist edge 48 and the front fastener 45. The umbilical cover anchor 66 is adapted to engage the front fastener 45 and maintain the umbilical cover in the anchored position. The diaper 10 also includes two stabilizers 74 located generally parallel with and proximate to the lines of weakness 60. The stabilizers 74 extend from the front waist edge 48 to the front fastener 45. In alternative embodiments, the stabilizers 74 may be non-parallel relative to the front waist edge 48 and/or the lines of weakness 60. The umbilical cover 64 is defined by portions of the front waist edge 48, the two lines of weakness 60 and portions of the edge of the front fastener 45 nearest the front waist edge 48.

Figure 13:
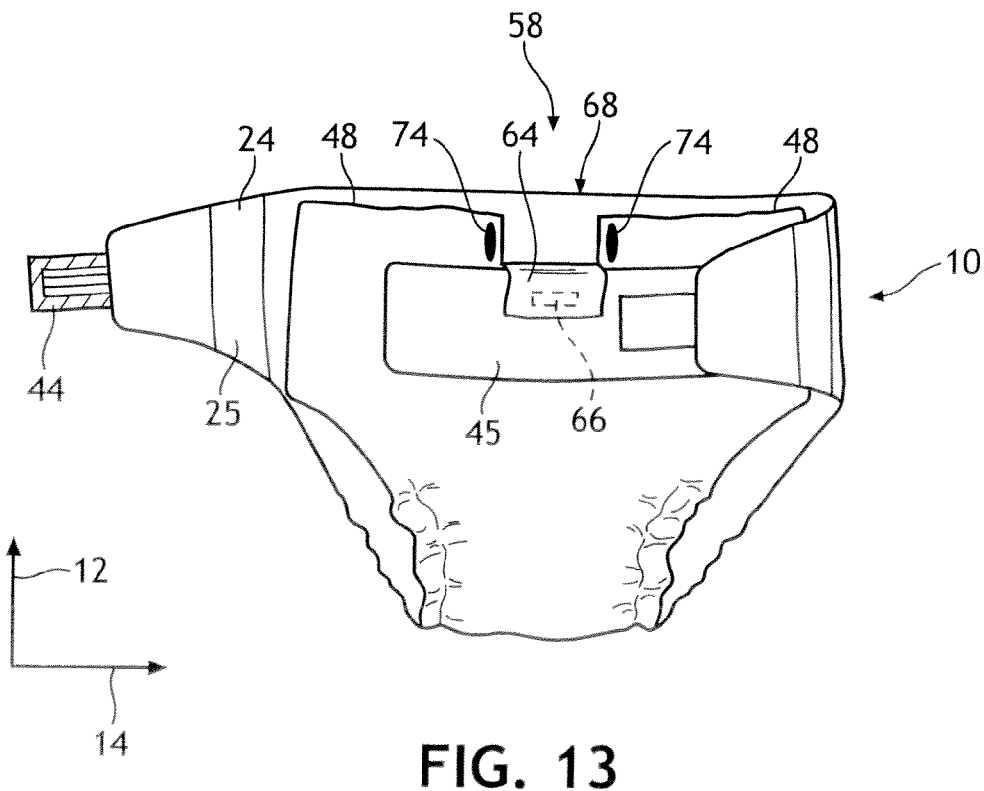
FIG. 13 representatively illustrates a front perspective view of the absorbent article of FIG. 12 with the umbilical feature in the opened condition.

Referring now to FIG. 13, the diaper 10 of FIG. 12 is shown in a partially fastened condition with the umbilical feature 58 in the opened condition. A caregiver desiring to utilize the umbilical feature 58 of diaper 10 may tear the diaper 10 along the lines of weakness 60 from the front waist edge 48 to the front fastener 45. Tearing the lines of weakness 60 allows the rectangular-shaped umbilical cover 64 to be moved from the starting position to the anchored position. The caregiver may then engage the umbilical cover anchor 66 with the front fastener 45 thereby maintaining the umbilical cover 64 in the anchored position and the umbilical feature 58 in the open condition. The stabilizers 74 are adapted to maintain the front waist edge 48 generally in the position shown thereby resisting rollover of the front waist edge 48 before and after the lines of weakness 60 are torn.

Figure 14:
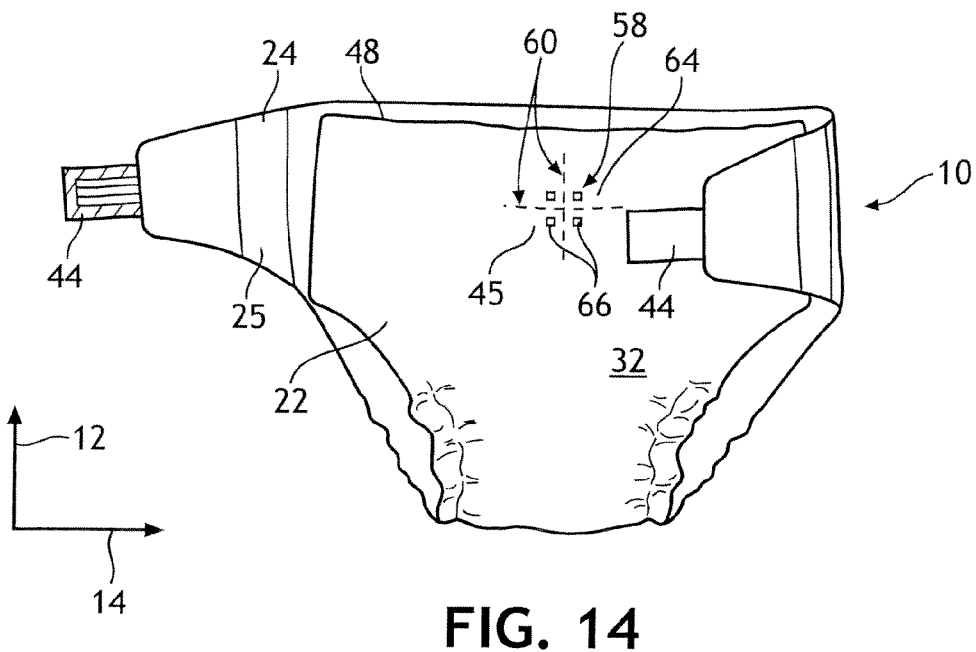
FIG. 14 representatively illustrates a front perspective view of a partially fastened absorbent article with the umbilical feature in the closed condition.

Referring now to FIG. 14, a diaper 10 is shown in a partially fastened condition. The back fasteners 44 are joined to the back ears 25 in the back portion 24. The back ears 25 are wrapped around and joined with the front fastener 45 located in the front portion 22 to maintain the diaper generally in the position shown. In this embodiment, the outer cover 32 is adapted to function as the front fastener 45 as is known in the art. For example, the outer cover 32 may function as the loop portion of a hook and loop fastening system. The diaper 10 also includes an umbilical feature 58 that includes two lines of weakness 60 intersecting one another at approximately right angles, four umbilical cover anchors 66 and four umbilical covers 64. The umbilical feature 58 is illustrated in the closed condition and the umbilical covers 64 are illustrated in the starting position.

The umbilical feature 58 is located in the front portion 22 of the diaper 10. The umbilical feature 58 includes two lines of weakness 60. One line of weakness 60 extends generally in the longitudinal direction 12 and is generally centered in the lateral direction 14 of the diaper 10. This line of weakness 60 is illustrated as stopping short of the front waist edge 48 but in various embodiments may extend to the front waist edge 48. The other line of weakness 60 extends generally in the lateral direction 14. The two lines of weakness 60 intersect at approximately the midpoints such that a generally symmetric "plus" shape (+) is formed. Each line of weakness 60 is about 20 to 40 mm in length.

The umbilical feature 58 also includes four umbilical cover anchors 66. One umbilical cover anchor 66 is located in each quadrant and near the point of intersection of the generally symmetric plus-shape formed by the intersecting lines of weakness 60. The umbilical cover anchors 64 are illustrated as separate pieces of material joined with the outercover 32. In various embodiments the umbilical cover anchors 66 may be covered with umbilical cover tabs 80 to shield the umbilical cover anchors 66 and to provide a means for grasping and tearing the diaper 10 along the lines of weakness 60.

Figure 15:
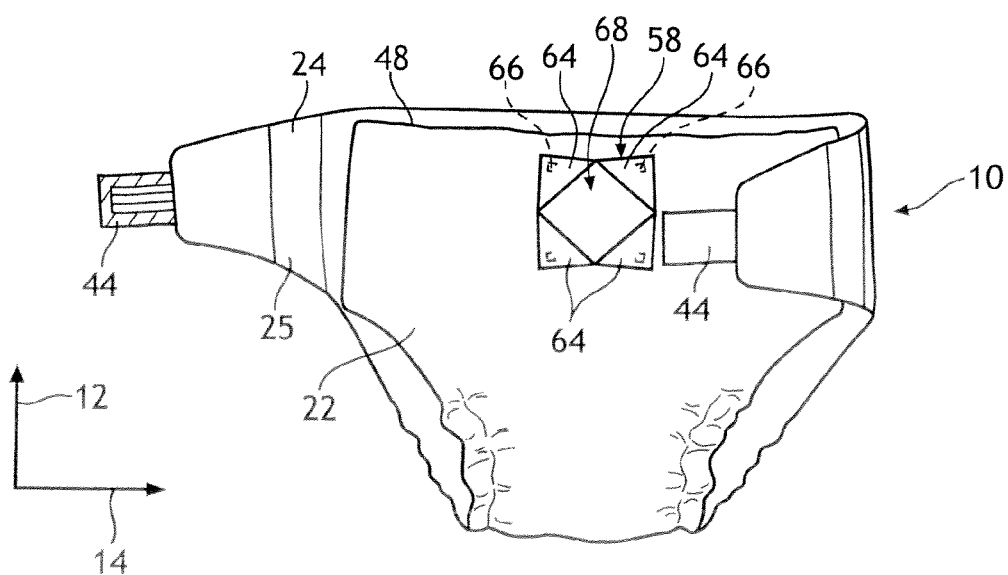
FIG. 15 representatively illustrates a front perspective view of the absorbent article of FIG. 14 with the umbilical feature in the opened condition.

Referring now to FIG. 15, the diaper 10 of FIG. 14 is shown in a partially fastened condition with the umbilical feature 58 in the opened condition. A caregiver desiring to utilize the umbilical feature 58 may tear the diaper 10 along the two lines of weakness 60 allowing four umbilical covers 64, each with an umbilical cover anchor 66 joined thereto, to be moved from the starting position to the anchored position. The umbilical cover anchors 66 are adapted to join with the front fastener 45, which in this embodiment is the outer cover 32, to maintain the umbilical feature 58 in the open condition. The umbilical feature 58 defines an umbilical relief area 68 when in the open condition.

Referring now to FIG. 16, a diaper 10 is shown in a partially fastened condition. The back fasteners 44 are joined to the back ears 25 in the back portion 24. The back ears 25 are wrapped around and joined with the front fastener 45 located in the front portion 22 to maintain the diaper generally in the position shown. The diaper 10 also includes an umbilical feature 58 that includes two lines of weakness 60, one umbilical cover anchor 66, one umbilical cover 64 and three fold lines 62. The fold lines 62 are depicted as dot-dash lines. In this embodiment, the umbilical cover anchor 66 is a pocket formed by an unbonded portion 54 of the front fastener 45 located between two bonded potions 56. The front fastener 45 is joined to the outer cover 32 at the bonded portions 56 in the front portion 22 via adhesive, ultrasonic bonding, thermal bonding, pressure bonding, or the like and combinations thereof. In alternative embodiments, the umbilical cover anchor 66 may be one or more pockets formed by an unbonded portion of the front waist elastic located between two bonded portions of the front waist elastic.

The umbilical feature 58 is illustrated in the closed condition and the umbilical cover 64 is illustrated in the starting position. The diaper 10 also has a pair of triangular-shaped stabilizers 74 located laterally outboard of the lines of weakness 60 in the corners formed by the lines of weakness 60 and the front waist edge 48. The stabilizers 74 are illustrated as being joined with the outercover 32, but, in various embodiments, may be joined with the front fastener 45, the front waist elastic 40, the bodyside liner 30, or combinations thereof.

The lines of weakness 60 extend from the front waist edge 48 to the front fastener 45 generally in the longitudinal direction 12. The lines of weakness 60 are approximately equidistant from the center of the diaper 10 and define the width of the umbilical cover 64. In this embodiment, the front fastener 45 has an unbonded portion 54 that defines a pocket that is adapted to be used as an umbilical cover anchor 66. The pocket is generally centered in the lateral direction 14 of the diaper 10 and is wider in the lateral direction 14 than the width of the umbilical cover 64 to allow the umbilical cover 64 to be tucked, at least in part, into the unbonded portion 54.

The three fold lines 62 extend generally in the lateral direction 14 from one line of weakness 60 to the other line of weakness 60. The three fold lines 62 are generally parallel to one another and are spaced equidistant from the front waist edge 48 to the front fastener 45. However, in various embodiments, the spacing may be non-equidistant.

Figure 17:
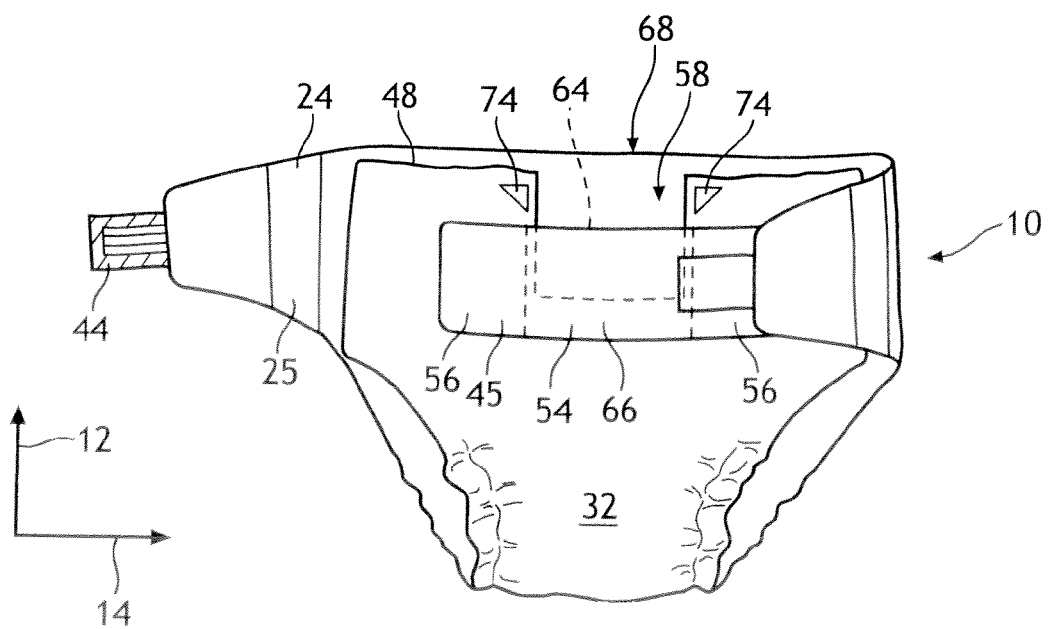
FIG. 17 representatively illustrates a front perspective view of the absorbent article of FIG. 16 with the umbilical feature in the opened condition.

Referring now to FIG. 17, the diaper 10 of FIG. 16 is shown in a partially fastened condition with the umbilical feature 58 in the opened condition thereby defining an umbilical relief area 68. A caregiver desiring to utilize the umbilical feature 58 may tear the diaper 10 along the lines of weakness 60 to allow the umbilical cover 64 to move from the starting position to the anchored position. The umbilical cover 64 is defined by the torn edges that were previously along the lines of weakness 60, portions of the front waist edge 48 and portions of the edge of the front fastener 45 closest to the front waist edge 48. The caregiver may then tuck a portion of the umbilical cover 64 in the pocket formed by the unbonded portion 54 located between the bonded portions 56 and between the front fastener 45 and the outer cover 32. The umbilical cover anchor 66 is adapted to receive the umbilical cover 64, anchor the umbilical cover 64 in the anchored position and maintain the umbilical feature 58 in the open condition thereby creating an umbilical relief area 68.

In this embodiment, the diaper 10 may be torn along the lines of weakness 60. The caregiver may determine the relative size of the umbilical cover 64 by the distance, in the longitudinal direction 12 and from the front waist edge 48, by which the lines of weakness 60 are separated. The caregiver may then move the umbilical cover 64 from the starting position to the anchored position and fold the umbilical cover 64 along one of the fold lines 62. If the fold line 62 nearest the front waist edge 48 is utilized, the umbilical cover 64 will be smaller and the umbilical relief area 68 will be smaller as compared to the situation wherein one of the other fold lines 62, which are more remote from the front waist edge 48, are utilized. The anchored position is maintained by tucking at least a portion of the umbilical cover 64 between the front fastener 45 and the outer cover 32 in the unbonded portion 54 or pocket.

Figure 18:
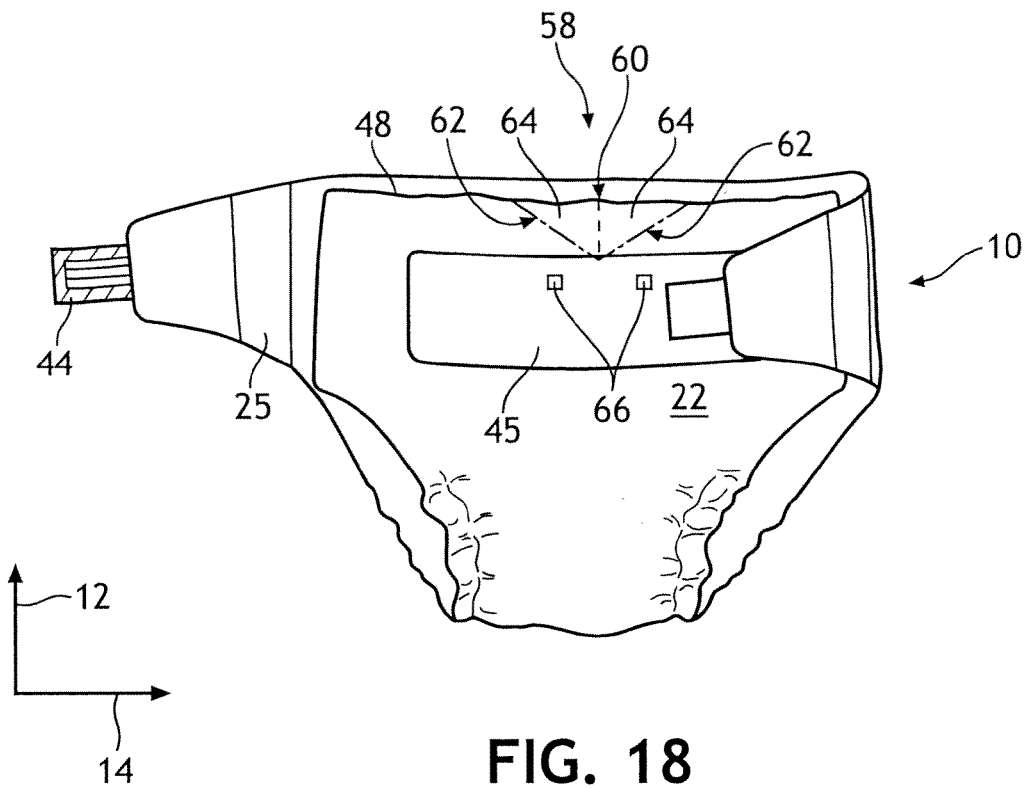
FIG. 18 representatively illustrates a front perspective view of a partially fastened absorbent article with the umbilical feature in the closed condition.

Referring now to FIG. 18, a diaper 10 is shown in a partially fastened condition. The back fasteners 44 are joined to the back ears 25 in the back portion 24. The back ears 25 are wrapped around and joined with the front fastener 45 located in the front portion 22 to maintain the diaper generally in the position shown. The diaper 10 also includes an umbilical feature 58 that includes a line of weakness 60, two fold lines 62, two umbilical cover anchors 66, and two umbilical covers 64. The umbilical cover anchors 66 are permanently joined with, and located on, the front fastener 45. The umbilical feature 58 is illustrated in the closed condition and the two umbilical covers 64 are illustrated in the starting position.

The line of weakness 60 extends in the longitudinal direction 12 from the front waist edge 48 to the front fastener 45. The line of weakness 60 is generally centered in the lateral direction 14. The two fold lines 62 extend from the front waist edge 48 to the end of the line of weakness 60 that is proximate the front fastener 45. The fold lines 62 form approximately a 30 degree angle with the front waist edge 48, but can be at various angles in various embodiments. The smaller the angle formed between the fold lines 62 and the front waist edge 48, the larger the resulting umbilical relief area 68. The two umbilical cover anchors 66 are permanently joined to the front fastener 45 and are positioned such that at least a portion the each umbilical cover 64 will contact at least one umbilical cover anchor 66 after the diaper 10 is torn along the line of weakness 60 and is folded along the folding lines 62.

Figure 19:
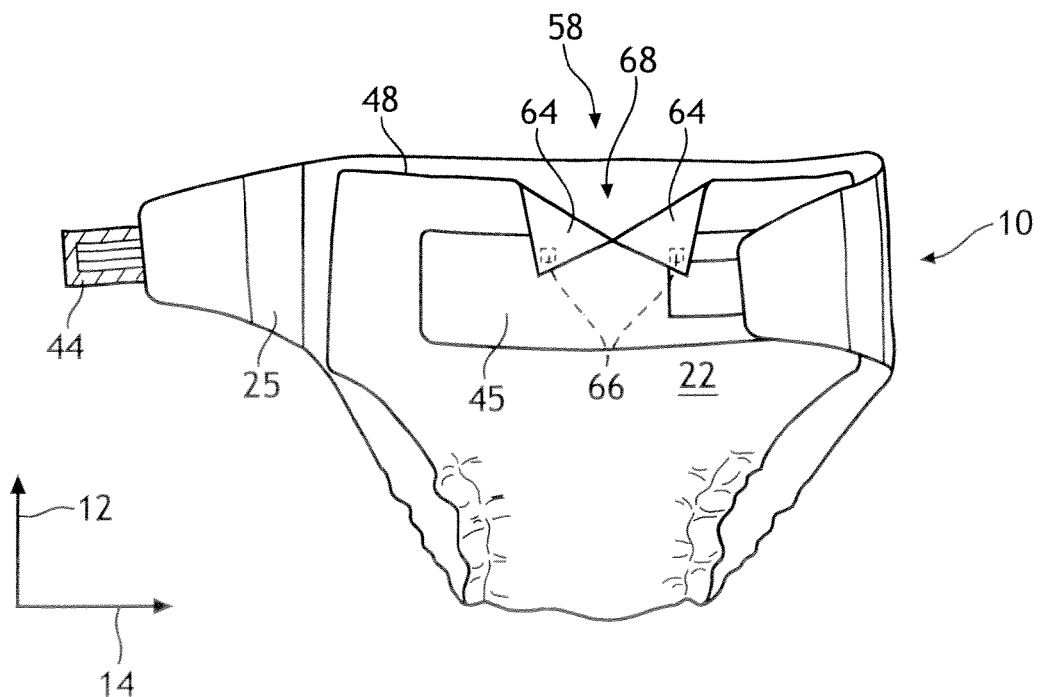
FIG. 19 representatively illustrates a front perspective view of the absorbent article of FIG. 18 with the umbilical feature in the opened condition.

Referring now to FIG. 19, the diaper 10 of FIG. 18 is shown in a partially fastened condition with the umbilical feature 58 in the opened condition and the umbilical covers 64 in the anchored position. A caregiver desiring to utilize the umbilical feature 58 of FIG. 18 may tear the diaper 10 along the line of weakness 60 from the front waist edge 48 to the front fastener 45 thus allowing the two umbilical covers 64 to be moved from the starting position to the anchored position. The movement of the umbilical covers 64 can occur along the fold lines 62. The umbilical cover 64 may be maintained in the anchored position by engaging the umbilical cover 64 with the umbilical cover anchors 66 as illustrated in FIG. 19. The umbilical feature 58 is in the open position and defines an umbilical relief area 68.

The present invention also includes a method of providing a system to create an umbilical relief area in a diaper. The method includes providing any of the embodiments disclosed herein. The method further includes providing instructions to a caregiver to tear the diaper along the at least one line of weakness, to move the at least one umbilical cover from the starting position to the anchored position and to maintain the umbilical cover in the anchored position by utilizing the at least one umbilical cover anchor.

In various embodiments, the method may further include providing instructions to a caregiver to move the at least one umbilical cover from the starting position to the anchored position by folding along the at least one fold line.

In various embodiments, the method may further include providing instructions to a caregiver to locate the at least one fold line by using at least one folding guide.

In various embodiments, the method may further include providing instructions to a caregiver to locate the at least one line of weakness by using at least one line of weakness indicator.

While the invention has been described in detail with respect to specific embodiments thereof, it will be appreciated that those skilled in the art, upon attaining an understanding of the foregoing will readily conceive of alterations to, variations of and equivalents to these embodiments. Accordingly, the scope of the present invention should be assessed as that of the appended claims and any equivalents thereto.

The invention claimed is:

1. A diaper comprising,
   a. an outer cover;
   b. a liner;
   c. an absorbent core positioned between the outer cover and the liner;
   d. a front portion having a first line of weakness adapted to be torn, the first line of weakness comprising one or more rows of perforations;
   e. a first umbilical cover defined in part by the first line of weakness, the first umbilical cover being moveable from a starting position to an open position upon tearing the diaper at the first line of weakness; and
   f. at least one of a front fastener joined to the outer cover in the front portion and a front waist elastic joined to the liner in the front portion, the at least one of the front fastener and the front waist elastic having at least two bonded portions and at least one unbonded portion, the at least one unbonded portion being located between the at least two bonded portions and defining a first pocket, the first pocket adapted to accept and maintain at least a portion of the first umbilical cover in the open position.

2. The diaper of claim 1 wherein the diaper includes the front fastener joined to the outer cover in the front portion and the at least one unbonded portion defines the first pocket between the front fastener and the outer cover.

3. The diaper of claim 1 wherein the diaper includes the front waist elastic joined to the liner in the front portion and the at least one unbonded portion defines the first pocket between the front waist elastic and the liner.

4. The diaper of claim 1 further comprising a second umbilical cover, the second umbilical cover being moveable from a starting position to an open position upon tearing the diaper at the first line of weakness.

5. The diaper of claim 4 wherein the second umbilical cover is defined at least in part by the first line of weakness.

6. The diaper of claim 4 wherein the at least one of the front fastener and the front waist elastic has a further bonded portion and a second unbonded portion, the further bonded portion being laterally spaced from the at least two bonded portions, the second unbonded portion being located between the further bonded portion and the at least two bonded portions and defining a second pocket.

7. The diaper of claim 6 wherein the second pocket is adapted to accept and maintain at least a portion of the second umbilical cover in the open position.

8. The diaper of claim 1 wherein the front portion has a second line of weakness adapted to be torn.

9. The diaper of claim 8 wherein the second line of weakness further defines the first umbilical cover.

10. The diaper of claim 1 further comprising at least one fold line and at least one folding guide.

11. The diaper of claim 1 wherein the front portion further comprises a front waist edge and a pair of stabilizers located proximate the front waist edge.

12. A diaper comprising,
    a. an outer cover;
    b. a liner;
    c. an absorbent core positioned between the outer cover and the liner;
    d. a front portion having a line of weakness adapted to be torn, the line of weakness comprising at least one row of perforations;
    e. a pair of umbilical covers defined in part by the line of weakness, the umbilical covers being moveable from a starting position to an open position upon tearing the diaper at the line of weakness; and
    f. a front fastener located in the front portion, the front fastener having umbilical cover anchors joined thereto, the umbilical cover anchors adapted to maintain the umbilical covers in the open position.

13. The diaper of claim 12 further comprising at least one fold line.

14. The diaper of claim 13 further comprising at least one folding guide.

15. The diaper of claim 12 further comprising at least one line of weakness indicator.

16. The diaper of claim 12 wherein the umbilical cover anchors comprise a discrete piece of hook material.

* * * * *